US00RE50083E

(19) United States
(12) Reissued Patent
Shi et al.

(10) Patent Number: US RE50,083 E
(45) Date of Reissued Patent: *Aug. 20, 2024

(54) URAT1 INHIBITOR AND USE THEREOF

(71) Applicant: Jiangsu Atom Bioscience and Pharmaceutical Co., Ltd., Zhenjiang (CN)

(72) Inventors: Dongfang Shi, Fremont, CA (US); Changjin Fu, Zhenjiang (CN); Xi Cheng, Zhenjiang (CN); Jianghua Zhu, Zhenjiang (CN); Jie Gu, Zhenjiang (CN)

(73) Assignee: Jiangsu Atom Bioscience and Pharmaceutical Co., Ltd., Zhenjiang (CN)

( * ) Notice: This patent is subject to a terminal disclaimer.

(21) Appl. No.: 17/707,795

(22) Filed: Mar. 29, 2022

Related U.S. Patent Documents

Reissue of:

(64) Patent No.: 10,875,865
Issued: Dec. 29, 2020
Appl. No.: 16/461,298
PCT Filed: Nov. 15, 2017
PCT No.: PCT/CN2017/111013
§ 371 (c)(1),
(2) Date: May 15, 2019
PCT Pub. No.: WO2018/090921
PCT Pub. Date: May 24, 2018

(30) Foreign Application Priority Data

Nov. 16, 2016 (CN) ..... 201611008935.X
Nov. 13, 2017 (CN) ..... 201711115037.9

(51) Int. Cl.

| | |
|---|---|
| ***C07D 487/04*** | (2006.01) |
| ***A61P 3/00*** | (2006.01) |
| ***C07D 307/80*** | (2006.01) |
| ***C07D 471/04*** | (2006.01) |
| ***C07D 491/048*** | (2006.01) |
| ***C07D 513/04*** | (2006.01) |

(52) U.S. Cl.
CPC ..... *C07D 487/04* (2013.01); *A61P 3/00* (2018.01); *C07D 307/80* (2013.01); *C07D 471/04* (2013.01); *C07D 491/048* (2013.01); *C07D 513/04* (2013.01)

(58) Field of Classification Search
CPC .. C07D 487/04; C07D 307/80; C07D 471/04; C07D 491/048; C07D 513/04; C07D 491/04; A61P 3/00; A61P 19/06; A61K 31/343; A61K 31/429; A61K 31/437; A61K 31/4985; A61K 31/519; A61K 31/19
See application file for complete search history.

(56) References Cited

U.S. PATENT DOCUMENTS 4,400,387 A † 8/1983 Rosseels
10,399,971 B2 * 9/2019 Shi ..... C07D 471/04
2011/0028467 A1 † 2/2011 Ahn

FOREIGN PATENT DOCUMENTS

EP 0061380 A1 * 9/1982 ..... C07D 487/04

OTHER PUBLICATIONS

Moog et al. "Bicyclic imidazo derivatives, a new class of highly selective inhibitors for the human immunodeficiency virus type 1" Antiviral Research, 1994, vol. 24, pp. 275-288.*
Locuson et al. "Quantitative Binding Models for CYP2C9 Based on Benzbromarone Analogues" Biochemistry, 2004, vol. 43, No. 22, pp. 6948-6958.*
Ye et al., "Medicinal Chemistry", 1st edition, pp. 66-67, "3.3 Optimization of Lead Compounds" published in Jun. 2012 by Zhejiang University Press, Hangzhou, China.†
Ma et al., "Medicinal Chemistry", 1st edition, pp. 6-7, "Bioisosterism" published in Jul. 2007 by Henan Science and Technology Press, Zhengzhou, China.†
Xu et al., "3-[(1S,2S,3R)-2,3-Difluoro-1-hydroxy-7-methylsulfonylindan-4-yl]oxy-5-fluorobenzonitrile (PT2977), a Hypoxia-Inducible Factor 2α (HIF-2α) Inhibitor for the Treatment of Clear Cell Renal Cell Carcinoma" J. Med. Chem. 62, 6876-6893, published on Jun. 24, 2019 by American Chemical Society, Washington D.C.†
Wempe et al., Human uric acid transporter 1 (hURAT1) an inhibitor structure activity relationship (SAR) Study, Nucleossides, Nucleotides and Nucleic Acids, 30:12, 1312-1323, published in 2011 by Taylor and Francis Group, LLC, London.†

* cited by examiner
† cited by third party

*Primary Examiner* — Jerry D Johnson
(74) *Attorney, Agent, or Firm* — Sheppard Mullin Richter & Hampton LLP

(57) ABSTRACT

Disclosed are a class of URAT1 inhibitor compounds and the use of such compounds. These compounds are compounds represented by the structure of formula (I) or pharmaceutically acceptable salts thereof. Experiments show that the compounds provided by the present invention have a very good inhibitory effect on hURAT1-transported uric acid in HEK293 transfected cells, and show that such compounds have a good potential for application in the treatment of hyperuricemia or gout.

20 Claims, No Drawings

URAT1 INHIBITOR AND USE THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD OF THE INVENTION

The invention belongs to the field of medicinal chemistry and particularly relates to a class of URAT1 inhibitor compounds and applications in medicine.

BACKGROUND OF THE INVENTION

Uric acid is the final product of purine metabolism in the human body. Due to the absence of rasburicase in the human body, serum uric acid (sUA) cannot be further degraded and excessive sUA needs to be excreted out of the human body through the kidney and intestinal tract. The kidney is the main organ for about 70% excretion of uric acid, out of the human body. Therefore, the transport capacity for uric acid in the kidney can directly manage the sUA. Due to the disorder of purine metabolism leading to the increasing of sUA or excessive intake of high-purine food and insufficient renal elimination of uric acid, a large amount of sUA accumulate, which leads to hyperuricemia. Generally, hyperuricemia is defined as sUA concentration higher than 7 mg/dL for men and 6 mg/dL for women. About 80% to 85% of hyperuricemia patients are caused by insufficient renal elimination of uric acid leading to accumulation of sUA (Cheeseman C. Solute carrier family 2, member 9 and uric acid homeostasis. Current Opinion in Nephrology and Hypertension, 2009, 18(5):428-432). When the concentration of sUA is saturated, urate crystals are deposited in joints, tendons, kidneys and other human tissues, in which is gout (Richette P, Bardin T. Gout. Lancet. 2010, 375(9711): 318-328). Gout will cause urate nephropathy and uric acid nephrolithiasis, leading to renal insufficiency. Meanwhile, gout and hyperuricemia are significantly and positively correlated with diseases such as hyperlipidemia, hypertension, diabetes and atherosclerosis (Rho Y H, Woo J H, Choi S J, et al. Association between serum uric acid and the adult treatment panel III-defined metabolic syndrome: results from a single hospital database. Metabolism. 2008, 57:(1) 71-76). Gout and hyperuricemia seriously affect people's health and quality of life.

Gout is the second largest metabolic disease following diabetes and has been listed as one of 20 stubborn diseases in the 21$^{st}$ century by the United Nations. With the improvement of people's living standard and the extension of people's average lifetime, the incidence of hyperuricemia and gout are on the rise. Gout has an incidence of approximately 1%-2% in the worldwide. The incidence in the developed countries is relatively high, as a survey of 2007-2008 reported there were about 8.3 million of gout patients in the US. The incidence of gout in the United Kingdom and Germany had reached 1.4% in 2000 to 2005 (Annemans L, Spaepen E, Gaskin M, et al. Gout in the UK and Germany: prevalence, comorbidities, and management in general practice 2000-2005. Annals of the Rheumatic Diseases, 2008, 67(7): 960-966). In China, the incidence of gout has increased dramatically in the past decade. It is reported that the number of gout patients in China has exceeded 50 million, and the number of men with gout is much higher than that of women. An epidemiological study on 3978 persons aged from 40 to 74 in Shanghai urban areas, carried out in 2010, showed that about 25% of men suffer from hyperuricemia (Raquel Villegas, Xiang Y B, Cai Q Y, et al. Prevalence and determinants of hyperuricemia in middle-aged, urban Chinese men. Metabolic Syndrome and Related Disorders, 2010, 8(3): 263-270). About 5% to 12% of hyperuricemia patients would eventually develop into gout (Peng Jianbiao, Sun Piaoyang. Cycloalkyl acid derivative, preparation method thereof, and pharmaceutical application thereof. Shanghai Hengrui Pharm Co., Ltd. WO2014183555A1).

The medicines for the treatment of acute attack of gout mainly include colchicine, non-steroidal anti-inflammatory drugs (NSAIDs), adrenocorticotropic hormone, and glucocorticoid. Colchicine has a good efficacy to treat acute gout attack, but has severe adverse reactions, such as diarrhea, vomiting and abdominal pain spasm. Many NSAIDs have severe gastrointestinal adverse reactions. These drugs can only termporarily relieve the pain of the patients, and cannot reduce the concentration of sUA and eliminate urate deposition in the body.

In order to treat gout fundamentally, sUA must be controlled at the normal level by sUA-lowering medications. Magagement of the level of sUA is a long-term treatment, and mainly includes the following two approaches: inhibiting the production of uric acid and promoting the excretion of uric acid.

Xanthine oxidase, as an enzyme for the metabolism of nucleotides in the body, is a key enzyme for the generation of uric acid. Uric acid producing inhibitors can effectively lower the level of sUA by inhibiting the function of xanthine oxidase to reduce the production of uric acid. The more often used drugs are allopurinol and uloric. Allopurinol is one of the xanthine oxidase inhibitors. It needs to be used in high dose, and for some people can cause severe skin erythema multiforme, which is sometime fatal. It is often accompanied by liver injury and other side effects. Another xanthine oxidase inhibitor is called uloric (febuxostat), which was launched in Europe and the US in 2009. Uloric also has very serious side effects such as cardiovascular problem and gastrointestinal discomfort, and it may cause headaches and liver injury. Gout patients cannot reach to the normal level of sUA by febuxostat for a long term treatment.

Another major approach to treat gout is to promote the excretion of uric acid. The mechanism involves the inhibition of uric acid transport by human urate anion transporter 1 (hURAT1) located in the proximal tubular epithelial cell membrane to reduce the reabsorption of uric acid in kindeys and increase the renal excretion of uric acid. As the most important uric acid reabsorption protein in the human body, hURAT1 is specifically expressed on brush border membranes of epithelial cells of human renal proximal convoluted tubule and controls more than about 90% of uric acid reabsorption after glomerular filtration (Wempe M F, Jutabha P, Quade B, et al. Developing potent human uric acid transporter 1 (hURAT1) inhibitors. Journal of Medicinal Chemistry. 2011, 54: 2701-2713). The hURAT1 is encoded by the SLC22A12 gene which has several mutations that cause uric acid metabolism abnormally. A Meta-analysis showed that this gene has 0.13% variables contributed to sUA level (So A, Thorens B. Uric acid transport and disease. Journal of Clinical Investigation, 2010, 120(6): 1791-1799).

Currently, marketed uricosuric medications d for gout treatment are URAT1 inhibitors, included Benzbromarone, Zurampic, probenecid and sulfinpyrazone. Zurampic from AstraZeneca had been approved to treat gout with a combination with allopurinol in a dose of 200 mg/day by the United States in December 2015 and Europe in February 2016, respectively. But its efficacy is far less than that of benzbromarone. In addition, FDA requires that its severe renal toxicity should be highlighted with a black box warning in the specifications. This drug also has very severe cardiovascular toxicity and other side effects. Both probenecid and sulfinpyrazone are uricosuric agents with high does administration in poor efficacy and bad side effects.

Benzbromarone as the URAT1 inhibitor is still widely used in the market for the treatment of gout. Its chemical name is (3,5-dibromo-4-hydroxy-'phenyl)(2-ethylbenzofuran-3-yl)-methanone, which was developed by France Snaofi-Synthelabo company and launched in 1976. But the use of benzbromarone has not been approved in the US and was withdrawn from the market in most European countries in 2003 due to its severe liver toxicity. (Jansen T L, Reinders M K, van Roon E N, et al. Benzbromarone withdrawn from the European market: another case of "absence of evidence is evidence of absence". Clinical Experimental Rheumatology, 2004, 22(5):651). Another disadvantage of this drug is that it has a strong inhibitory effect on the CYP2C9 of P450s enzymes, resulting in liver injury and drug-drug interactions. However, more than 20 countries, such as China, Germany, Japan, Brazil and New Zealand still widely use it because of the lack of good gout drugs on the market.

Studies have shown that the fulminant or fatal liver injury of benzbromarone has been associated with its reactive metabolites. A possible mechanism of liver toxicity may involve the bioactivation of benzbromarone through sequential hydroxylation of the benzofuran ring to form 6-hydroxybenzbromarone and a catechol by CYP2C9, which can be further oxidized by P450s enzymes to a reactive quinone metabolite capable of adducting thiol reagents/cysteine residues. (Matthew G. McDonald M G, Rettie A E. Sequential metabolism and bioactivation of the hepatotoxin benzbromarone: formation of glutathione adducts from a catechol intermediate. Chemical Research in Toxicology. 2007, 20 (12):1833-1842). Benzbromarone also has other side effects, such as diarrhea, stomach discomfort, nausea, macula, flush, itching, and so on.

Currently, the compounds for gout treatment in clinical trials include the URAT1 inhibitor RDEA-3170 from AstraZeneca in Phase II clinical trials, and the products from Pfizer, BioCryst Pharmaceutical Company, LG life Sciences in Korea, Cymabay Theraoeutics, JW Pharmaceutical, Chugai Pharmaceutical, Fuji Yakuhin and Sanwa Kagaku are also at Phase I or II clinical trials. The URAT1 inhibitor developed by Jiangsu Hengrui Pharmaceutical Company has entered Phase I clinical trials in China, and its chemical structure has the certain similarity to the two compounds from AstraZeneca. However, most of these compounds still show the poor efficacy and severe toxicity.

Currently, there are only a few drugs for gout treatment at the worldwide, and these drugs generally have the disadvantages of poor efficacy, severe side effects. Therefore, it is very important to develop gout drugs that are highly effective and have low toxicity.

SUMMARY OF INVENTION

The objective of the present invention is to provide a series of new compounds based on the current technologies, aiming to obtain a URAT1 inhibitor with low toxicity and good efficacy for the treatment of hyperuricemia or gout. The tests result showed that the compounds provided by this invention have a very good inhibitory effect on hURAT1 transport uric acid in HEK293 transfected cells, indicating that the compounds have a good application prospect in the treatment of hyperuricemia or gout.

The object of the invention can be achieved by the following measures:

Provided is a compound of Formula (I)

(I)

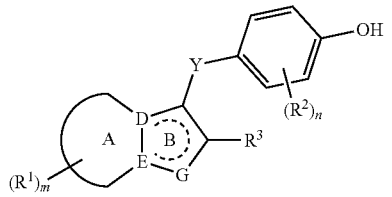

or a pharmaceutically acceptable salt thereof, wherein:

Ring A is a five-membered aromatic ring containing a hetero atom, or a six-membered aromatic ring;

Ring B is a five-membered aromatic ring containing two nitrogen atoms, or a furan ring;

D is C or N;

E is C or N;

G is N or O, and G is O when both D and E are C;

Y is carbonyl, sulfur, sulfone, sulfoxide, optionally substituted methylene or imino; when D or E in the ring A is N atom such that the ring A forms a pyridine ring, or when the ring A is a benzene ring, Y is not a carbonyl group;

$R^1$ is hydrogen, deuterium, hydroxy, halogen, nitro, amino, cyano, $C_{1-3}$ alkyl, substituted $C_{1-3}$ alkyl, substituted $C_{1-3}$ amino, $C_{1-3}$ alkoxy or substituted $C_{1-3}$ alkoxy;

$R^2$ is hydrogen, deuterium, hydroxy, halogen, nitro, amino, cyano, $C_{1-3}$ alkyl, substituted $C_{1-3}$ alkyl, substituted $C_{1-3}$ amino, $C_{1-3}$ alkoxy or substituted $C_{1-3}$ alkoxy;

$R^3$ is $C_{1-4}$ alkyl, substituted $C_{1-4}$ alkyl or halogen;

m is an integer from 0 to 3;

n is an integer from 1 to 3;

One or two hetero atoms in the ring A is/are selected from the group consisting of N, S or O, and the substituent in the group Y is selected from the group consisting of hydroxyl, amino, cyano, carboxyl, $C_{1-3}$alkoxy or $C_{1-3}$ alkyl, the substituent in the group $R^1$, $R^2$ or $R^3$ is selected from the group consisting of hydroxyl, halogen, nitro, amino or cyano.

In one embodiment, the ring A is a benzene ring, a pyridine ring, a pyrimidine ring, a pyrazine ring, a triazole ring, an imidazole ring, a thiazole ring, or an oxazole ring, an oxadiazole ring or a thiadiazole ring, the B ring is an imidazole ring, a pyrazole ring or a furan ring; when D or E in the ring A is N such that the ring A forms a pyridine ring, or the ring A is a benzene ring, Y is not a carbonyl group.

In another embodiment, the present invention is selected from the compounds shown by the structures of formula (II), formula (III), formula (IV) or formula (V), or pharmaceutically acceptable salts thereof.

(II)

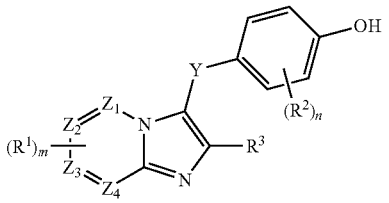

-continued (III)

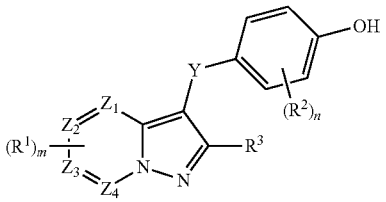

(IV)

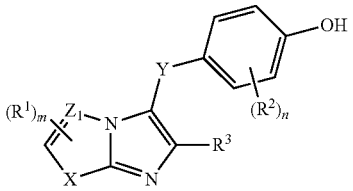

(V)

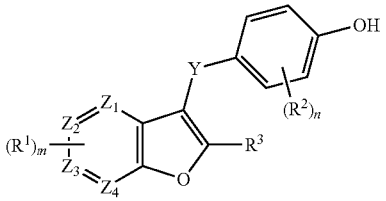

Wherein $Z_1$, $Z_2$, $Z_3$ or Z4 is each independently CH or N; X is S, O or $NR^4$; $R^4$ is H, —$CH_3$ or —$CH_2CH_3$; in formulas (II), (III) and (V) When $Z_1$, $Z_2$, $Z_3$ and $Z_4$ are all CH, Y is not a carbonyl group.

In a preferred embodiment, the invention is selected from the compounds shown by the structures described below, or pharmaceutically acceptable salts thereof, (II-A)

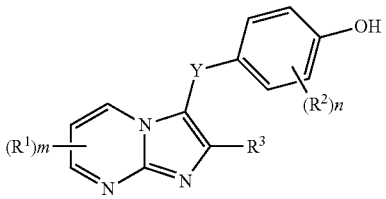

(II-B)

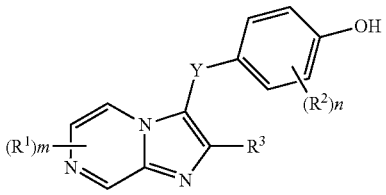

(II-C)

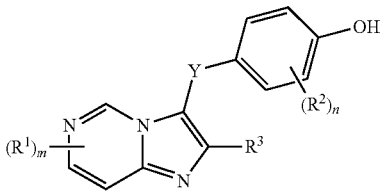

-continued (II-D)

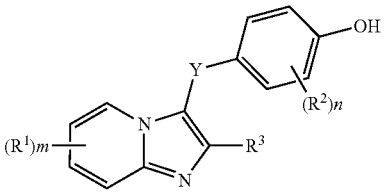

(III-A)

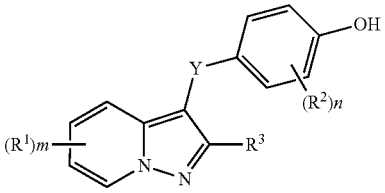

(IV-A)

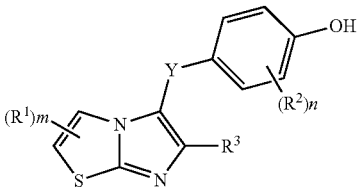

(IV-B)

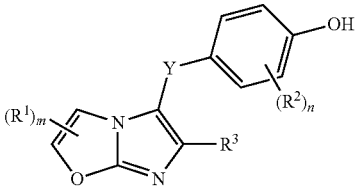

(IV-C)

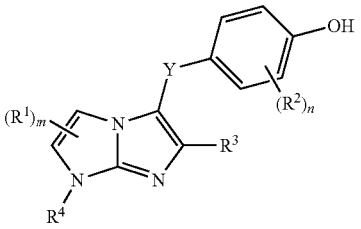

(IV-D)

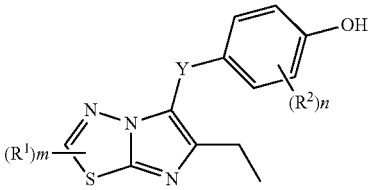

(V-A)

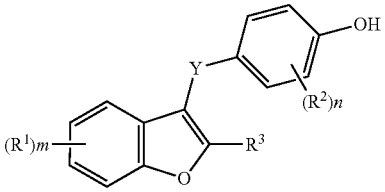

-continued (V-B)

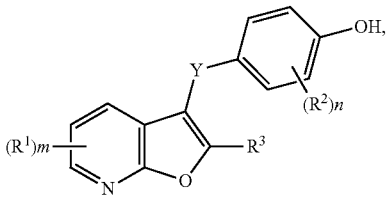

In the formula (II-D) and the formula (III-A), Y is not a carbonyl group.

In a preferred embodiment, in the formulas above, Y is CH—OH, CH—$NH_2$, CH—CN, NH(imino), $NCH_3$ or CO(carbonyl) group, and $R^3$ is $C_{2-3}$ alkyl; in formula (II-D) and formula (III-A), Y is not a carbonyl group.

In a preferred embodiment, $R^1$ is hydrogen, deuterium, hydroxy, halogen, nitro, amino, cyano, $C_{1-3}$ alkyl, $C_{1-3}$ haloalkyl, $C_{1-3}$ alkoxy or $C_{1-3}$ haloalkoxy, and m is 0, 1 or 2.

In a preferred embodiment, $R^2$ is hydrogen, halogen, nitro, cyano, $C_{1-3}$ alkyl, $C_{1-3}$haloalkyl, and n is 1 or 2.

In a more preferred embodiment, provided are the compounds or pharmaceutically acceptable salts thereof according to the present invention, wherein the compounds are selected from the group consisting of:

(3,5-dibromo-4-hydroxyphenyl)(2-ethylimidazo[1,2-a]pyrimidine-3-yl)methanone;

(3,5-dibromo-4-hydroxyphenyl)(2-ethylimidazo[2,1-b]thiozole-5-yl)methanone;

(3,5-dibromo-4-hydroxyphenyl)(2-ethylimidazo[1,2-a]pyrazine-3-yl)methanone;

3-bromo-5-[(2-ethylimidazo[1,2-a]pyridine-3-yl)hydroxymethyl]-2-hydroxybenzonitrile;

5-[(2-ethylimidazo[1,2-a]pyridine-3-yl)hydroxymethyl]-2-hydroxybenzonitrile;

2,6-dibromo-4-[(6-ethylimidazo[2,1-b]thiozole-5-yl)hydroxymethyl]phenol;

2,6-dibromo-4-[(2-ethylimidazo[1,2-a]pyrazine-3-yl)hydroxymethyl]phenol;

2-bromo-4-[(2-ethyl-6-fluoroimidazo[1,2-a]pyridine-3-yl)hydroxymethyl]-6-fluorophenol;

2,6-dibromo-4-[(2-ethyl pyrazolo[1,5-a]pyridine-3-yl)hydroxymethyl]phenol;

2,6-dibromo-4-[(6-bromo-2-ethylimidazo[1,2-a]pyridine-3-yl)hydroxymethyl]phenol;

2,6-dibromo-4-{[(-2-ethyl-7-(trifluoromethyl)imidazo[1,2-a]pyridine-3-yl)]hydroxymethyl}phenol;

2,6-dibromo-4-[(2-ethylbenzofuran-3-yl)hydroxymethyl]phenol;

2,6-dibromo-4-[(2-ethylimidazo[1,2-a]pyridine-3-yl)methyl]phenol;

(3,5-dibromo-4-hydroxyphenyl)(6-ethylimidazo[2,1-b][1,3,4]thiodiazole-5-yl)methanone;

2-bromo-4-(2-ethylimidazo[1,2-a]pyridine-3-yl)hydroxymethyl-6-methylphenol;

2,6-dibromo-4-[(2-ethylbenzofuran-3-yl)(methoxy)methyl]phenol;

2,6-dibromo-4-{(2-ethyl-7-methoxyimidazo[1,2-a]pyridine-3-yl)hydroxymethyl}phenol;

(3,5-dibromo-4-hydroxyphenyl)(2-propylfuro[2,3-b]pyridine-3-yl)methanone.

The preparation method of the compound of the present invention is given below:

Formula 1

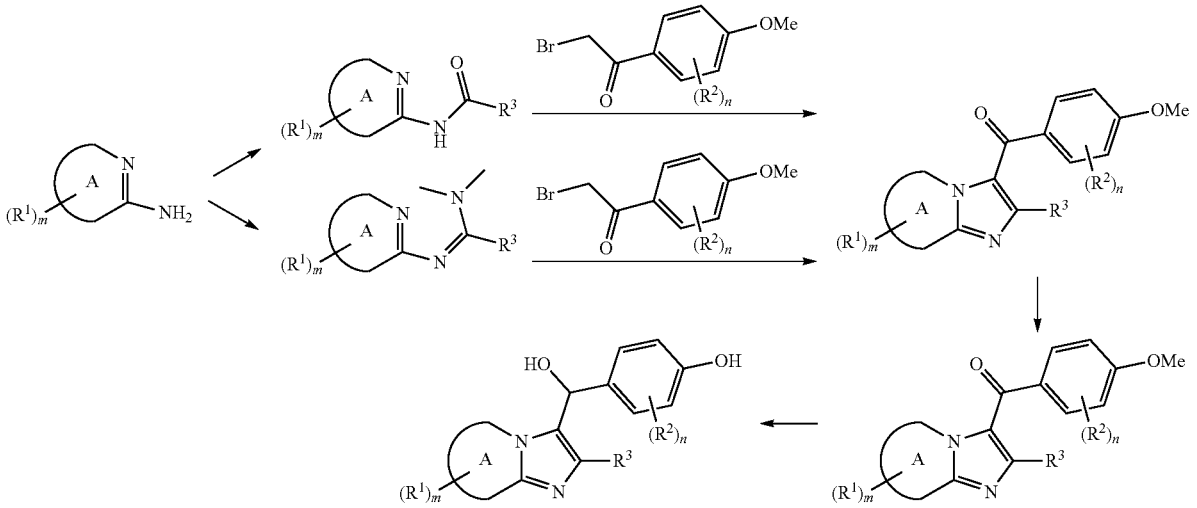

In the formula, an amino ring A (pyridine, pyrimidine, thiazole, pyrazine, etc.) compound is formed into an amide (or hydrazine) compound and then reacted with a substituted bromoacetophenone to give a corresponding imidazo ring A (pyridine, pyrimidine, thiazole, pyrazine or the like) compound which undergoes a demethylation, halogenation reaction, and/or reduction reaction or other reaction to give a corresponding target product.

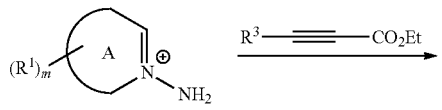

-continued

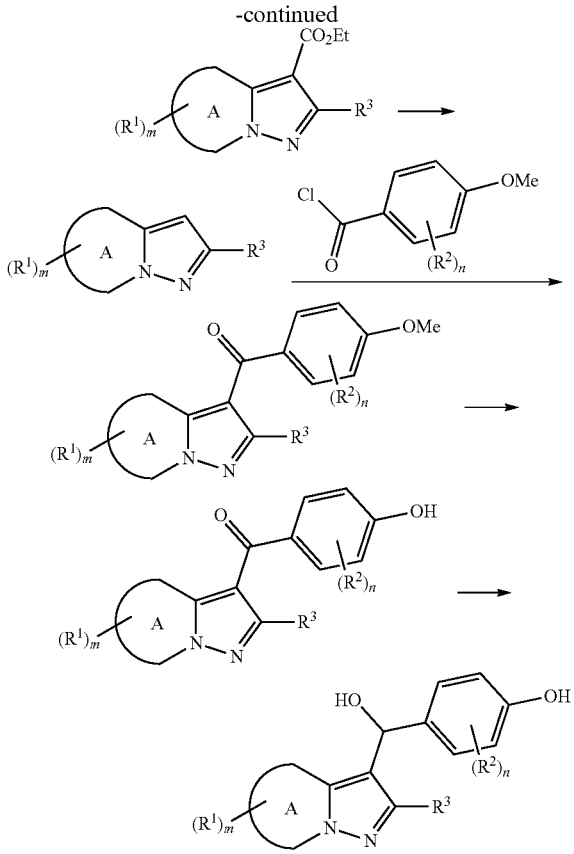

In the formula, the amino ring A (pyridine, pyrimidine, pyrazine, etc.) salt is subjected to a ring-closing reaction with alkyne to give a corresponding pyrazolo ring A (pyridine, pyrimidine, pyrazine, etc.) compound, the compound obtained after hydrolysis and decarboxylation is reacted with an acyl chloride under Lewis acid catalysis to give a diaryl ketone compound, which is subjected to demethylation, halogenation, and/or reduction or other reaction to give a corresponding target product.

The definition of each group in the synthesis method is described above.

Unless otherwise stated, the following terms used in the claims and the specifications have the following meanings:

The "five-membered aromatic ring" refers to a conjugated, planar ring-structured fused ring group composed of five ring atoms, which is aromatic and the ring atom may be an atom other than a carbon atom, i.e., hetero atom. When the five-membered aromatic ring contains a hetero atom, the hetero atom may be N, S or O, and the number of hetero atoms is not limited to one, and may be two, three or the like. The five-membered aromatic ring containing hetero atom(s) in the present invention includes, but is not limited to, a triazole ring, an imidazole ring, a thiazole ring, an oxazole ring, an oxadiazole ring or a thiadiazole ring, etc.

The "six-membered aromatic ring" refers to a conjugated, planar ring-structured fused ring group composed of six ring atoms, which is aromatic and the ring atom may be an atom other than a carbon atom, i.e., hetero atom. When the six-membered aromatic ring contains a hetero atom, the hetero atom may be N, S or O, and the number of hetero atoms is not limited to one, and may be two, three or the like. The six-membered aromatic ring containing hetero atom(s) in the present invention includes, but is not limited to, a pyridine ring, a pyrimidine ring, a pyrazine ring, etc.

"Hydrogen" means protium (1H), which is the main stable isotope of hydrogen.

"Deuterium" means a stable morphological isotope of hydrogen, also known as heavy hydrogen, and its elemental symbol is D.

"Halogen" means fluorine atom, chlorine atom, bromine atom or iodine atom.

"Alkyl" means a saturated $C_{1-20}$ aliphatic hydrocarbon group, including both straight-chain and branched-chain groups (the numerical ranges recorded in this application, such as "1-20", mean the group, when it is alkyl group, may contain 1 carbon atom, 2 carbon atoms, 3 carbon atoms, etc. up to 20 carbon atoms). An alkyl group having 1 to 4 carbon atoms is referred to as a lower alkyl group. When the lower alkyl group has no substituent, it is referred to as an unsubstituted lower alkyl group. More preferably, the alkyl group is a medium sized alkyl group having 2 to 5 carbon atoms. The alkyl group in the present invention is, for example, methyl, ethyl, propyl, 2-propyl, n-butyl, isobutyl, t-butyl or pentyl. Preferably, the alkyl group is a lower alkyl group having 1 to 4 carbon atoms, such as methyl, ethyl, propyl, 2-propyl, n-butyl, isobutyl or t-butyl. The alkyl group can be substituted or unsubstituted.

"Alkoxy" means an —O— (unsubstituted alkyl) group and an —O— (unsubstituted cycloalkyl) group, which further denotes —O— (unsubstituted alkyl). Representative examples include, but are not limited to, methoxy, ethoxy, propoxy, butoxy, cyclopropoxy, cyclobutoxy, cyclopentyloxy, cyclohexyloxy, and the like.

"Carbonyl" means C═O.

"Sulfone group" means —$S(O)_2$—.

"Thionylene group" means —S(O)—.

"Methylene" means —$CH_2$—.

"Imino" means —NH—.

"Hydroxy" means —OH.

"Nitro" means —$NO_2$.

"Amino" means —$NH_2$.

"Carboxy" means —COOH.

"Cyano" means —CN.

A "pharmaceutically acceptable salt" is a salt comprising a compound of formula (I) with an organic or inorganic acid, meaning those salts which retain the biological effectiveness and properties of the parent compound. Such salts include:

(1) an acid addition salt obtained by reaction of a free base of a parent compound with an inorganic or organic acid such as, but not limited to, hydrochloric acid, hydrobromic acid, nitric acid, phosphoric acid, metaphosphoric acid, sulfuric acid, sulfurous acid and perchloric acid, etc., organic acid such as, but not limited to, acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, succinic acid or malonic acid.

(2) a salt obtained by replacing an acidic proton in a parent compound with a metal ion or by complexing with an organic base, the metal ion is, such as an alkali metal ion, an alkaline earth metal ion or an aluminum ion, the organic base is, such as ethanolamine, diethanolamine, triethanolamine, tromethamine, N-methylglucamine, and the like.

A "pharmaceutical composition" means a mixture of one or more of the compounds described herein or their pharmaceutically acceptable salts and prodrugs with other chemical ingredients, such as pharmaceutically acceptable carriers and excipients. The purpose of the pharmaceutical composition is to facilitate the administration of the compound to the organism.

Hereinafter, unless otherwise specified, the compounds of the formula (I) as active ingredients of the therapeutic agents including all pharmaceutically acceptable salts thereof, are to be understood as falling within the scope of the invention, In the present specification, they are simply referred to as "compounds of the formula (I)" for convenience only.

The present invention includes a pharmaceutical composition comprising, a compound of any one of the present invention as an active ingredient, a pharmaceutically acceptable salt thereof, or a readily hydrolyzable prodrug thereof, and as well as a pharmaceutically acceptable excipient.

Each compound of the present invention or a pharmaceutically acceptable salt thereof has low toxicity and good medicinal effect, and can be used for the manufacture of a medicament for promotion of uric acid excretion, in particular, for treatment or prevention of hyperuricemia or gout. Experiments show that the compounds provided by the present invention have a very good inhibitory effect on hURAT1 transport uric acid in HEK293 transfected cells, indicating that the compounds have a good application prospect in the treatment of hyperuricemia or gout.

DETAILED DESCRIPTION OF THE INVENTION

The present invention will be further described below by embodiments, but the scope of the present invention is not limited to the following embodiments.

Embodiment 1: Synthesis of (3,5-dibromo-4-hydroxyphenyl)(2-ethylimidazo[1,2-a]-pyrimidine-3-yl)methanone (4)

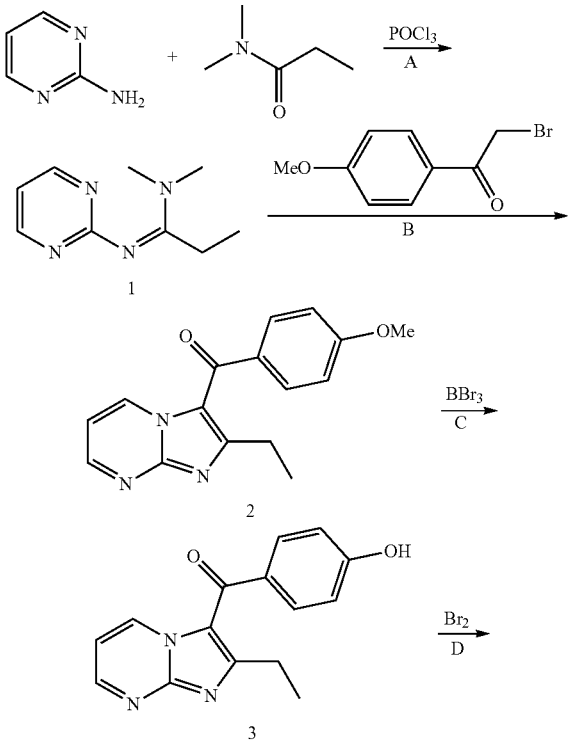

-continued

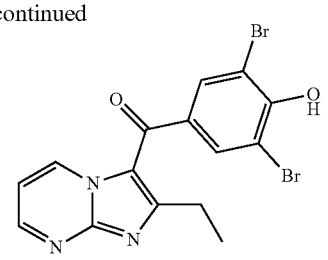

4

Step A: A mixture of 2-aminopyrimidine (570 mg, 6.0 mmol), phosphorus oxychloride (4.6 g, 30.0 mmol), N,N-dimethylpropionamide (910 mg, 9.0 mmol) and methylbenzene (15 mL) was stirred for 2 h at 110° C. The reaction mixture was cooled to room temperature, then poured into ice water (60 mL) and adjusted with 2 M sodium hydroxide aqueous solution until the pH value was 8-9. The mixture was extracted with ethyl acetate (40 mL×5) and dried with anhydrous sodium sulfate. The solvent was evaporated under reduced pressure, and the product was purified by flash chromatography (200-300 meshes of silica gel, eluted with ethyl acetate:petroleum ether=1:1 to 20:1) to obtain N,N-dimethyl-N'-(pyrimidine-2-yl)-propanimidamide (1) (250 mg). The yield was 23.4%.

Step B: A mixture of the compound 1 (240 mg, 1.35 mmol), 2-bromo-1-(4-methoxyphenyl)ethanone (308 mg, 1.35 mmol) and DMF (10 mL) was stirred for 2 h at room temperature, then heated to 60° C. and continuously stirred for 1.5 h. The mixture was cooled to room temperature, added with water (40 mL), adjusted with saturated sodium carbonate aqueous solution until the pH value was 7-8, and extracted with ethyl acetate (40 mL×3). The combined organic phase was successively washed with water (20 mL) and brine (20 mL), and then dried with anhydrous sodium sulfate. The solvent was evaporated under reduced pressure, and the product was purified by flash chromatography (200-300 meshes of silica gel, eluted with ethyl acetate: petroleum ether=1:4 to 2:5) to obtain (2-ethylimidazo[1,2-a]pyrimidine-3-yl)(4-methoxyphenyl)methanone (2) (190 mg). The yield was 50.0%. $^1$H NMR (DMSO-$d_6$, 400 MHz) δ 9.45-9.43 (m, 1H), 8.77-8.75 (m, 1H), 7.74 (dd, J=2.0, 6.8 Hz, 2H), 7.31-7.29 (m, 1H), 7.12 (dd, J=2.0, 6.8 Hz, 2H), 3.88 (s, 3H), 2.52-2.51 (m, 2H), 1.15 (t, J=7.6 Hz, 3H).

Step C: A solution of 1.0 M boron tribromide in methylbenzene (1.7 mL) was added dropwise into a solution of the compound 2 (120 mg, 0.427 mmol) in anhydrous dichloromethane (10 mL) in an ice-water bath, and the obtained mixture was stirred overnight at room temperature. The reaction mixture was poured into ice water (20 mL) and adjusted with saturated sodium bicarbonate aqueous solution until the pH value was 7-8. The mixture was extracted with ethyl acetate (30 mL×3) and dried with anhydrous sodium sulfate. The solvent was evaporated under reduced pressure, and the product was purified by flash chromatography (200-300 meshes of silica gel, eluted with ethyl acetate:petroleum ether:THF=1:5:1 to 5:5:1) to obtain (2-ethylimidazo[1,2-a]pyrimidine-3-yl)(4-hydroxyphenyl) methanone (3) (101 mg). The yield was 88.5%.

Step D: A solution of bromine (66 mg, 0.413 mmol) in acetic acid (2 mL) was added dropwise into a solution of the compound 3 (50 mg, 0.187 mmol) and sodium acetate (46 mg, 0.561 mmol) in acetic acid (5 mL), and the obtained mixture was stirred for 0.5 h at room temperature. Saturated sodium hydrogen sulfite aqueous solution was added dropwise into the reaction mixture until the color faded away. The solvent was evaporated under reduced pressure, and the reaction mixture was added with water (30 mL) and adjusted with saturated sodium bicarbonate aqueous solution until the pH value was 7-8. The mixture was extracted with ethyl acetate (40 mL×2) and dried with anhydrous sodium sulfate. The solvent was evaporated under reduced pressure, and the product was recrystallized with ethyl acetate/petroleum ether to obtain (3,5-dibromo-4-hydroxyphenyl)(2-ethylimidazo[1,2-a]pyrimidine-3-yl)methanone (4). $^1$H NMR (DMSO-d6, 400 MHz) δ 9.42 (dd, J=2.0, 6.8 Hz, 1H), 8.78 (dd, J=2.0, 7.6 Hz, 1H), 7.91 (s, 2H), 7.34-7.31 (m, 1H), 2.51-2.48 (m, 2H), 1.20 (t, J=7.6 Hz, 3H). MS (EI, m/z): 426.0 $[M+H]^+$.

Embodiment 2: Synthesis of (3,5-dibromo-4-hydroxyphenyl)(6-ethylimidazo[2,1-b]-thiazole-5-yl) methanone(8)

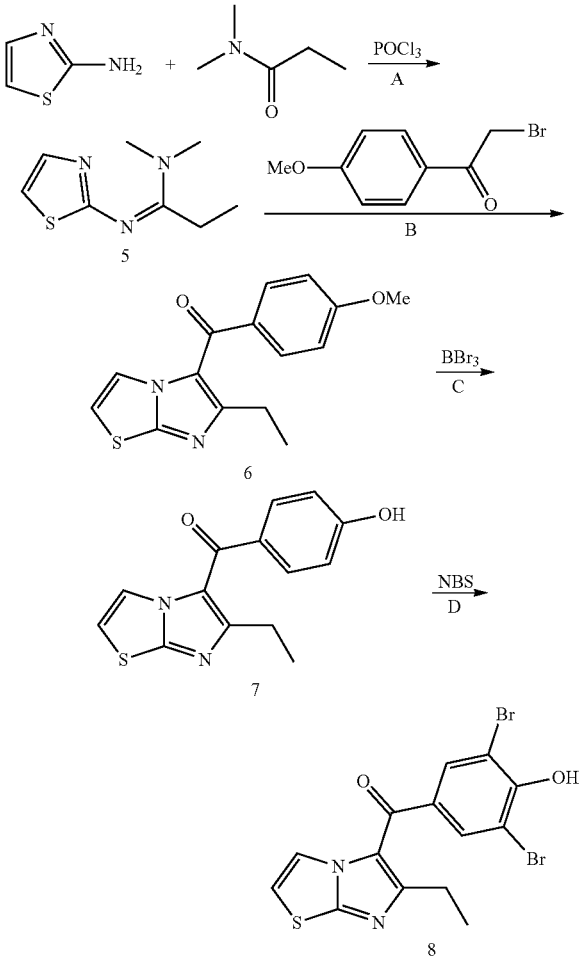

Step A: A mixture of 2-aminothiazole (600 mg, 6.0 mmol), phosphorus oxychloride (4.6 g, 30.0 mmol), N,N-dimethylpropionamide (910 mg, 9.0 mmol) and methylbenzene (15 mL) was stirred for 2 h at 110° C. The reaction mixture was cooled to room temperature, then poured into ice water (60 mL) and adjusted with 2 M sodium hydroxide aqueous solution until the pH value was 8-9. The mixture was extracted with ethyl acetate (40 mL×3), and the combined organic phase was successively washed with water (20 mL) and brine (20 mL) and dried with anhydrous sodium sulfate. The solvent was evaporated under reduced pressure to obtain N,N-dimethyl-N'-(thiazole-2-yl)propanimidamide (5) (890 mg). The yield was 80.9%.

Step B: A mixture of the compound 5 (439 mg, 2.40 mmol), 2-bromo-1-(4-methoxyphenyl)ethanone (604 mg, 2.64 mmol) and DMF (10 mL) was stirred for 1 h at the room temperature, then heated to 60° C. and continuously stirred for 5 h, and then heated to 130° C. and stirred overnight. The mixture was cooled to room temperature, added with water (40 mL), adjusted with saturated sodium carbonate aqueous solution until the pH value was 7-8, and extracted with ethyl acetate (40 mL×3). The combined organic phase was successively washed with water (20 mL) and brine (20 mL), and then dried with anhydrous sodium sulfate. The solvent was evaporated under reduced pressure, and the product was purified by flash chromatography (200-300 meshes of silica gel, eluted with ethyl acetate: petroleum ether=1:30 to 1:20) to obtain (6-ethylimidazo[2,1-b]thiazole-5-yl)-(4-methoxyphenyl)methanone (6) (311 mg). The yield was 45.3%. $^1$H NMR (DMSO-d6, 400 MHz) δ 8.14 (d, J=4.4 Hz, 1H), 7.70 (d, J=8.8 Hz, 2H), 7.45 (d, J=4.4 Hz, 1H), 7.09 (d, J=8.8 Hz, 2H), 3.87 (s, 3H), 2.45 (q, J=7.6 Hz, 2H), 1.10 (t, J=7.6 Hz, 3H).

Step C: A solution of 1.0 M boron tribromide in methylbenzene (1.6 mL) was added dropwise into a solution of the compound 6 (113 mg, 0.395 mmol) in anhydrous dichloromethane (10 mL) in an ice-water bath, and the obtained mixture was stirred overnight at room temperature. The reaction mixture was poured into ice water (20 mL) and adjusted with saturated sodium bicarbonate aqueous solution until the pH value was 7-8. The mixture was extracted with ethyl acetate (30 mL×3) and dried with anhydrous sodium sulfate. The solvent was evaporated under reduced pressure, and the product was purified by flash chromatography (200-300 meshes of silica gel, eluted with ethyl acetate:dichloromethane=1:2) to obtain (2-ethylimidazo[1,2-a]pyrimidine-3-yl)(4-hydroxyphenyl)-methanone (7) (39 mg). The yield was 36.3%.

Step D: NBS (48 mg, 0.270 mmol) was added into a solution of the compound 7 (37 mg, 0.136 mmol) in DMF (3 mL), and the obtained mixture was stirred for 0.5 h at room temperature. The mixture was added with water (20 mL) and filtered. The filter cake was washed with a large amount of water, and the obtained solid was dissolved with a mixed solvent of THF/ethyl acetate and dried with anhydrous sodium sulfate. The mixture was filtered with a silica gel pad to obtain (3,5-dibromo-4-hydroxyphenyl)(2-ethylimidazo[2,1-b]thiazole-5-yl)-methanone (8) (40 mg). The yield was 68.4%. $^1$H NMR (DMSO-d6, 400 MHz) δ 8.14 (d, J=4.4 Hz, 1H), 7.86 (s, 2H), 7.46 (d, J=4.4 Hz, 1H), 2.43 (q, J=7.6 Hz, 2H), 1.15 (t, J=7.6 Hz, 3H). MS (EI, m/z): 430.9 $[M+H]^+$.

Embodiment 3: Synthesis of (3,5-dibromo-4-hydroxyphenyl)(2-ethylimidazo[1,2-a]-pyrazine-3-yl) methanone (12)

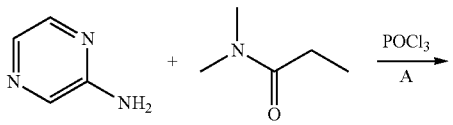

-continued

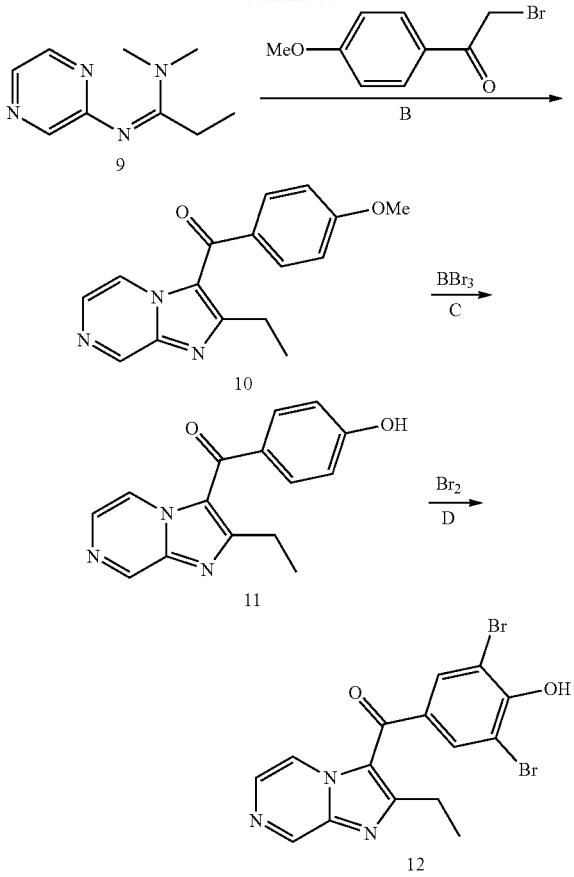

Step A: Triethylamine (4.68 g, 46.2 mmol) was added dropwise into a mixture of 2-aminopyrazine (2.0 g, 21.0 mmol), phosphorus oxychloride (4.84 g, 31.6 mmol), N,N-dimethylpropionamide (2.34 g, 23.1 mmol) and chloroform (20 mL) in an ice-water bath, and the obtained mixture was refluxed and stirred overnight. The reaction mixture was poured into ice water (60 mL) and adjusted with 2 M sodium hydroxide aqueous solution until the pH value was 8-9. The mixture was extracted with dichloromethane (50 mL×5), and the combined organic phase was washed with brine (30 mL) and dried with anhydrous sodium sulfate. Subsequently, the mixture was filtered by a short silica gel column, and the solvent was evaporated under reduced pressure to obtain N,N-dimethyl-N'-(pyrazine-2-yl)propanimidamide (9) (1.82 g). The compound was directly used in the next reaction without purification.

Step B: A mixture of the crude compound 9 (900 mg), 2-bromo-1-(4-methoxyphenyl)-ethanone (1.27 g, 5.54 mmol) and THF (25 mL) was stirred overnight at room temperature. The mixture was added with water (50 mL), adjusted with saturated sodium carbonate aqueous solution until the pH value was 7-8, and extracted with ethyl acetate (50 mL×3). The combined organic phase was successively washed with water (20 mL) and brine (20 mL) and dried with anhydrous sodium sulfate. The solvent was evaporated under reduced pressure, and the product was purified by flash chromatography (200-300 meshes of silica gel, eluted with ethyl acetate:petroleum ether=1:4 to 2:5) to obtain (2-ethylimidazo[1,2-a]pyrazine-3-yl)(4-methoxyphenyl) methanone (10) (160 mg). The total yield of the reactions in the steps A and B was 5.5%. $^1$H NMR (DMSO-d6, 400 MHz) δ 9.23 (d, J=1.2 Hz, 1H), 8.93-8.91 (m, 1H), 8.14 (d, J=4.8 Hz, 1H), 7.76 (dd, J=2.0, 6.8 Hz, 2H), 7.12 (dd, J=2.0, 6.8 Hz, 2H), 3.89 (s, 3H), 2.57 (q, J=7.6 Hz, 2H), 1.17 (t, J=7.6 Hz, 3H).

Experimental operations in steps C and D referred to the steps C and D in Embodiment 1 to obtain (3,5-dibromo-4-hydroxyphenyl)(2-ethylimidazo[1,2-a]pyrazine-3-yl)methanone (12). $^1$H NMR (DMSO-d6, 400 MHz): δ 9.11 (d, J=1.6 Hz, 1H), 8.59-8.58 (m, 1H), 7.98-7.97 (m, 1H), 7.72 (s, 2H), 2.71 (q, J=7.6 Hz, 2H), 1.27 (t, J=7.6 Hz, 3H). MS (EI, m/z): 426.0 $[M+H]^+$.

Embodiment 4: Synthesis of 3-bromo-5-[(2-ethylimidazo[1,2-a]pyridine-3-yl)-hydroxymethyl]-2-hydroxybenzonitrile (20)

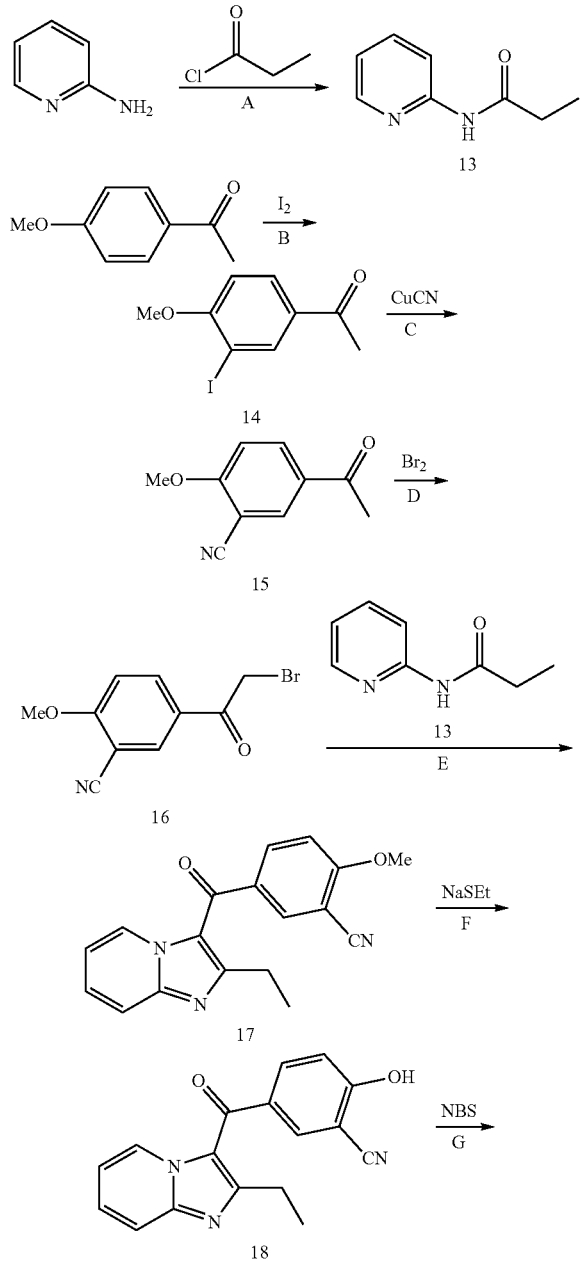

-continued

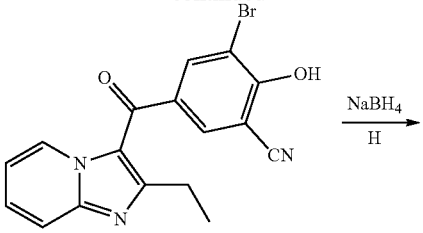

19

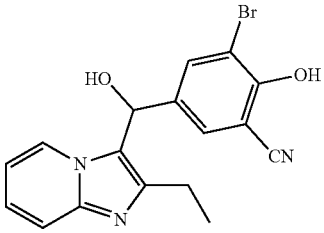

20

Step A: 2-aminopyridine (2.0 g, 21.3 mmol) and triethylamine (2.58 g, 25.5 mmol) were dissolved in dichloromethane (20 mL) and added dropwise with propionyl chloride (2.07 g, 22.4 mmol) in an ice-water bath, and the obtained mixture was warmed to room temperature automatically and stirred overnight. The mixture was added with water (40 mL) and extracted with dichloromethane (40 mL×3), and the combined organic phase was washed with brine (30 mL) and dried with anhydrous sodium sulfate. The solvent was evaporated under reduced pressure, and the product was purified by flash chromatography (200-300 meshes of silica gel, eluted with ethyl acetate:petroleum ether=1:15 to 1:10) to obtain N-(pyridine-2-yl)-propionamide (13) (2.74 g). The yield was 85.6%.

Step B: 4-methoxyacetophenone (44 g, 293 mmol) was added into a mixture of 1-chloromethyl-4-fluoro-1,4-diazabicyclo[2.2.2]octane bis(tetrafluoroborate) (104 g, 294 mmol), iodine (38.6 g, 152 mmol) and acetonitrile (440 mL) in an ice-water bath. After addition, the obtained mixture was stirred overnight at room temperature. The reaction mixture was added with water (1350 mL), and a large amount of solid was separated out. The mixture was filtered and dried to obtain 3-iodo-4-methoxyacetophenone (14) (70.0 g). The yield was 86.5%.

Step C: A mixture of the compound 14 (70.0 g, 254 mmol), cuprous cyanide (34.0 g, 380 mmol) and DMF (400 mL) was stirred overnight at 130° C. The mixture was cooled to room temperature, filtered with celite, added with water (1600 mL) and extracted with ethyl acetate (800 mL×3). The combined organic phase was successively washed with water (400 mL×2) and brine (400 mL), and then dried with anhydrous sodium sulfate. The solvent was evaporated under reduced pressure to obtain 5-acetyl-2-methoxybenzonitrile (15) (50.0 g). The compound was directly used in the next reaction without further treatment.

Step D: A solution of bromine (49.0 g, 307 mmol) in methanol (50 mL) was added dropwise into a solution of the crude compound 15 (45.0 g) in methanol (250 mL), and the obtained mixture was stirred overnight at room temperature. The mixture was added with water (900 mL), filtered and dried to obtain 5-(2-bromo-acetyl)-2-hydroxy-3-methylbenzonitrile(16) (41.0 g). The total yield of the reactions in the steps B and C was 70.6%.

Step E: A mixture of the compound 16 (41.0 g, 161 mmol), the compound 13 (24.0 g, 161 mmol) and methylbenzene (600 mL) was refluxed and stirred for 48 h. The mixture was cooled to room temperature, added with water (400 mL) and adjusted with saturated sodium bicarbonate solution until the pH value was 7-8. The mixture was extracted with ethyl acetate (600 mL×3) and dried with anhydrous sodium sulfate. The solvent was evaporated under reduced pressure, and the product was purified by flash chromatography (200-300 meshes of silica gel, eluted with ethyl acetate:petroleum ether=1:30 to 2:1) to obtain 5-(2-ethylimidazo[1,2-a]pyridine-3-carbonyl)-2-methoxybenzonitrile (17) (25.7 g). The yield was 52.3%.

Step F: 60% sodium hydride (4.8 g, 120 mmol) was added in portions into a solution of ethanethiol (8.4 mL) in THF (30 mL), the mixture was stirred for about 5 min and then filtered, and the filter cake was collected. Subsequently, the filter cake was added into a mixture containing the compound 17 (9.0 g, 29.5 mmol) and DMF (25 mL), and the obtained mixture was stirred for 2 h at 60° C. The mixture was cooled to room temperature, filtered with celite, added with water (100 mL) and adjusted with 2 M citric acid aqueous solution until the pH value was 5-6. The mixture was filtered, and the filter cake was recrystallized with acetonitrile to obtain 5-(2-ethylimidazo[1,2-a]pyridine-3-carbonyl)-2-hydroxybenzonitrile (18) (7.2 g). The yield was 83.8%.

Step G: NBS (5.28 g, 29.7 mmol) was added in portions into a solution of the compound 18 (7.2 g, 24.7 mmol) in DMF (70 mL), and the obtained mixture was stirred for 1 h at room temperature. The mixture was added with water (210 mL) and filtered, and the filter cake was washed with water (100 mL×3) and recrystallized with acetonitrile to obtain 3-bromo-5-(2-ethylimidazo[1,2-a]pyridine-3-carbonyl)-2-hydroxybenzonitrile (19) (7.0 g). The yield was 76.8%. $^1$H NMR (DMSO-d6, 300 MHz) δ 9.01 (d, J=6.9 Hz, 1H), 8.02 (s, 1H), 7.83 (s, 1H), 7.78-7.75 (m, 1H), 7.65-7.59 (m, 1H), 7.22-7.17 (m, 1H), 2.58-2.50 (m, 2H), 1.19 (t, J=7.2 Hz, 3H). MS (EI, m/z): 368.0 $[M-H]^-$.

Step H: Sodium borohydride (50 mg, 1.32 mmol) was added into a solution of the compound 19 (50 mg, 0.135 mmol) in methanol (5 mL), and the obtained mixture was stirred for 0.5 h at room temperature and added with sodium borohydride (50 mg, 1.32 mmol). The mixture was stirred for 0.5 h, added with water (20 mL), adjusted with 2 M citric acid aqueous solution until the pH value was 5-6, extracted with ethyl acetate/THF (7V/1V, 30 mLx3), and dried with anhydrous sodium sulfate. The solvent was evaporated under reduced pressure, and the product was purified by flash chromatography (200-30 meshes of silica gel, eluted with ethyl acetate:petroleum ether:THF=10:30:1 to 20:10:1) to obtain 3-bromo-5-[(2-ethylimidazo-[1,2-a]pyridine-3-yl) hydroxymethyl]-2-hydroxybenzonitrile (20). $^1$H NMR (DMSO-d6, 400 MHz) δ 8.18 (d, J=7.2 Hz, 1H), 7.66 (d, J=1.6 Hz, 1H), 7.52-7.50 (m, 2H), 7.24-7.20 (m, 1H), 6.84-6.82 (m, 1H), 6.33 (s, 1H), 6.23 (s, 1H), 2.71 (q, J=7.6 Hz, 2H), 1.24 (t, J=7.6 Hz, 3H). MS (EI, m/z): 372.1 $[M+H]^+$.

Embodiment 5: Synthesis of 5-[(2-ethylimidazo[1,2-a]pyridine-3-yl)hydroxymethyl]-2-hydroxybenzonitrile (21)

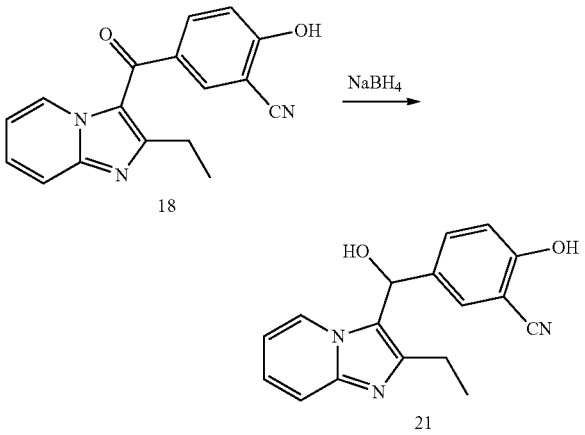

The compound 18 was used as raw material, and the method for preparing the compound 21 referred to the step H in Embodiment 4. $^1$H NMR (DMSO-d6, 400 MHz) δ 8.14 (d, J=6.8 Hz, 1H), 7.48-7.45 (m, 2H), 7.25-7.22 (m, 1H), 7.18-7.14 (m, 1H), 6.85-6.83 (m, 1H), 6.78-6.74 (m, 1H), 6.16 (s, 1H), 2.71 (q, J=7.6 Hz, 2H), 1.24 (t, J=7.6 Hz, 3H). MS (EI, m/z): 294.1 $[M+H]^+$.

Embodiment 6: Synthesis of 2,6-dibromo-4-[(6-ethylimidazo[2,1-b]thiazole-5-yl)-hydroxymethyl] phenol (22)

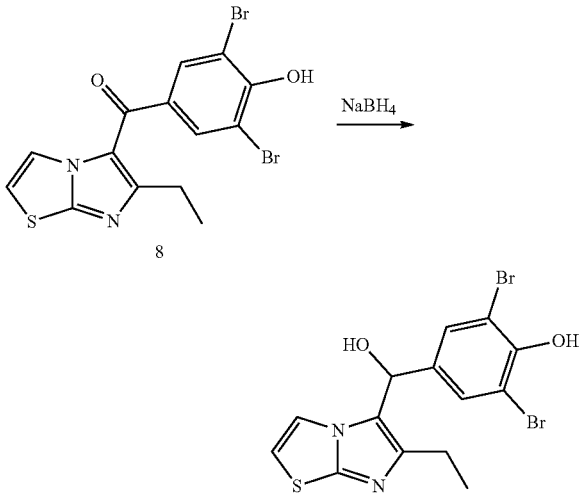

The compound 8 was used as raw material, and the method for preparing the compound 22 referred to the step H in Embodiment 4. $^1$H NMR (DMSO-d6, 400 MHz) δ 9.93 (s, 1H), 7.52 (d, J=4.8 Hz, 1H), 7.46 (s, 2H), 7.12 (d, J=4.4 Hz, 1H), 6.24 (s, 1H), 6.02 (s, 1H), 2.59 (q, J=7.6 Hz, 2H), 1.17 (t, J=7.6 Hz, 3H). MS (EI, m/z): 432.9 $[M+H]^+$.

Embodiment 7: Synthesis of 2,6-dibromo-4-[(2-ethylimidazo[1,2-a]pyrazine-3-yl)-hydroxymethyl] phenol (23)

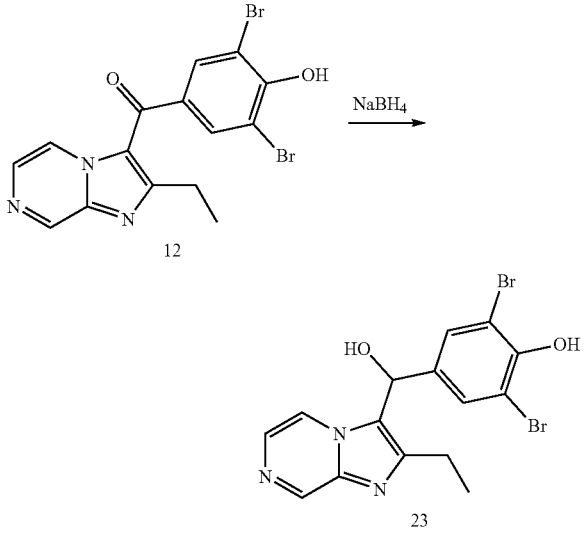

The compound 12 was used as raw material, and the method for preparing the compound 23 referred to the step H in Embodiment 4. $^1$H NMR (DMSO-d6, 400 MHz) δ 9.98 (s, 1H), 8.97 (d, J=1.2 Hz, 1H), 8.27-8.26 (m, 1H), 7.81 (d, J=4.4 Hz, 1H), 7.47 (s, 2H), 6.46 (d, J=4.4 Hz, 1H), 6.30 (d, J=4.0 Hz, 1H), 2.75 (q, J=7.6 Hz, 2H), 1.24 (t, J=7.6 Hz, 3H). MS (EI, m/z): 425.9 $[M-H]^-$.

Embodiment 8: Synthesis of 2-bromo-4-[(2-ethyl-6-fluoroimidazo[1,2-a]pyridine-3-yl)hydroxymethyl]-6-fluorophenol (28)

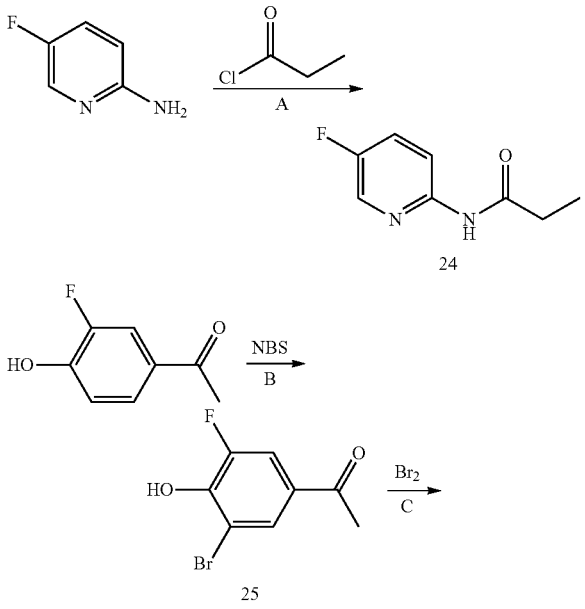

-continued

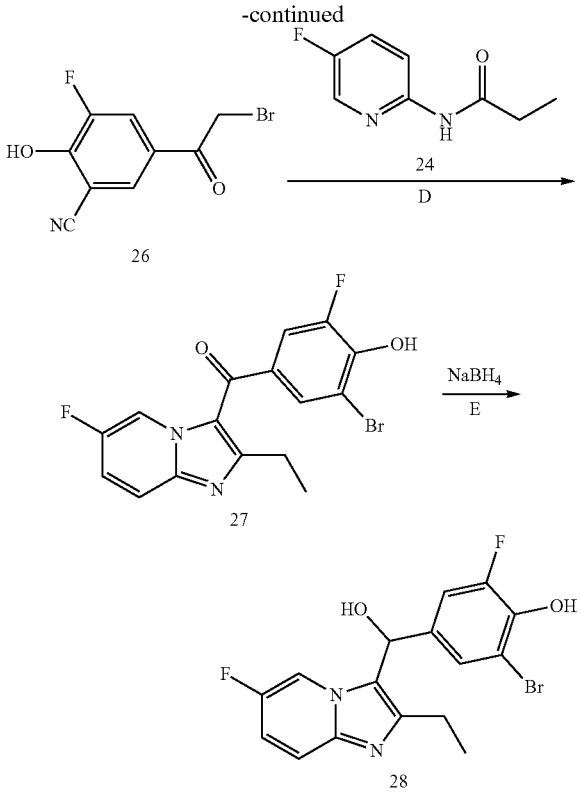

Step A: 2-amino-5-fluoropyridine (2.5 g, 22.3 mmol) and triethylamine (2.71 g, 26.8 mmol) were dissolved in dichloromethane (25 mL) and added dropwise with propionyl chloride (2.17 g, 23.5 mmol) in an ice-water bath, and the obtained mixture was warmed to room temperature automatically and stirred overnight. The mixture was added with water (40 mL) and extracted with dichloromethane (40 mL×3), and the combined organic phase was washed with brine (30 mL) and dried with anhydrous sodium sulfate. The solvent was evaporated under reduced pressure, and the product was purified by flash chromatography (200-300 meshes of silica gel, eluted with ethyl acetate:petroleum ether=1:5) to obtain N-(5-fluoropyridine-2-yl)-propionamide (24) (3.04 g). The yield was 81.1%.

Step B: NBS (977 mg, 5.49 mmol) was added in portions into a solution of 3-fluoro-4-hydroxyacetophenone (806 mg, 5.23 mmol) in DMF (10 mL), and the obtained mixture was stirred overnight at room temperature. The mixture was added with water (50 mL) and extracted with ethyl acetate (50 mL×3), and the combined organic phase was successively washed with water (30 mL×3) and brine (30 mL) and dried with anhydrous sodium sulfate. The solvent was evaporated under reduced pressure, and the product was recrystallized with petroleum ether/ethyl acetate to obtain 3-bromo-5-fluoro-4-hydroxyacetophenone (25) (1.0 g). The yield was 82.0%.

Step C: A solution of bromine (824 mg, 5.16 mmol) in methanol (5 mL) was added dropwise into a solution of the compound 25 (1.0 g, 4.29 mmol) in methanol (20 mL), and the obtained mixture was stirred overnight at room temperature. The mixture was added with water (60 mL) and extracted with ethyl acetate (60 mL×3), and the combined organic phase was washed with brine (30 mL) and dried with anhydrous sodium sulfate. The solvent was evaporated under reduced pressure, and the product was purified by flash chromatography (200-300 meshes of silica gel, eluted with ethyl acetate:petroleum ether=1:5) to obtain 2-bromo-1-(3-bromo-5-fluoro-hydroxyphenyl)ethanone (26) (940 mg). The yield was 70.2%.

Step D: A mixture of the compound 24 (210 mg, 1.25 mmol), the compound 26 (300 mg, 0.962 mmol) and N-methylpyrrolidone (10 mL) was stirred overnight at 150° C. The mixture was cooled to room temperature, added with water (50 mL), adjusted with saturated sodium bicarbonate aqueous solution until the pH value was 7-8, and adjusted with 2 M citric acid aqueous solution until the pH value was 5-6. The mixture was extracted with ethyl acetate (50 mL×3) and dried with anhydrous sodium sulfate. The solvent was evaporated under reduced pressure, and the product was purified by flash chromatography (200-300 meshes of silica gel, eluted with ethyl acetate:petroleum ether=1:25 to 1:5) to obtain (3-bromo-5-fluoro-4-hydroxyphenyl)(2-ethyl-6-fluoroimidazo[1,2-a]pyridine-3-yl)methanone(27). $^1$H NMR (DMSO-d6, 500 MHz) δ 11.44 (s, 1H), 9.24-9.22 (m, 1H), 7.88-7.85 (m, 1H), 7.75-7.71 (m, 2H), 7.63-7.60 (m, 1H), 2.47 (q, J=7.5 Hz, 2H), 1.18 (t, J=7.5 Hz, 3H). MS (EI, m/z): 379.0 $[M-H]^-$.

Step E: Sodium borohydride (80 mg, 2.11 mmol) and lithium chloride (14 mg, 0.330 mmol) were added into a solution of the compound 27 (80 mg, 0.210 mmol) in methanol (10 mL), and the obtained mixture was stirred for 2.5 h at 35° C. The mixture was added with water (20 mL), adjusted with 2 M citric acid aqueous solution until the pH value was 5-6, and extracted with ethyl acetate (30 mL×3). The combined organic phase was washed with brine (20 mL) and dried with anhydrous sodium sulfate. The mixture was filtered by a short silica gel pad, the solvent was evaporated under reduced pressure, and the product was recrystallized with ethyl acetate/petroleum ether to obtain 2-bromo-4-[(2-ethyl-6-fluoroimidazo[1,2-a]pyridine-3-yl)-hydroxymethyl]-6-fluorophenol (28). $^1$H NMR (DMSO-d6, 400 MHz) δ 10.43 (s, 1H), 8.27-8.25 (m, 1H), 7.59-7.56 (m, 1H), 7.31-7.25 (m, 2H), 7.15-7.12 (m, 1H), 6.33 (d, J=4.0 Hz, 1H), 6.21 (d, J=4.0 Hz, 1H), 2.66 (q, J=7.6 Hz, 2H), 1.21 (t, J=7.6 Hz, 3H). MS (EI, m/z): 383.0 $[M+H]^+$.

Embodiment 9: Synthesis of 2,6-dibromo-4-[(2-ethylpyrazolo[1,5-a]pyridine-3-yl)-hydroxymethyl] phenol (35)

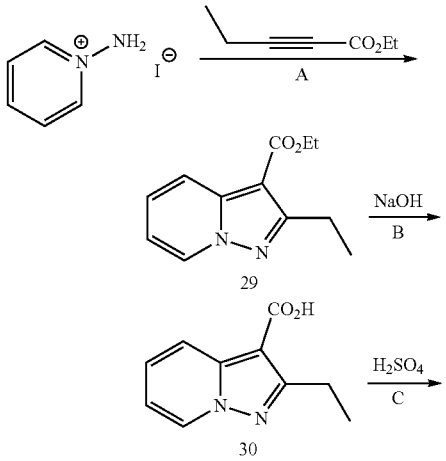

-continued

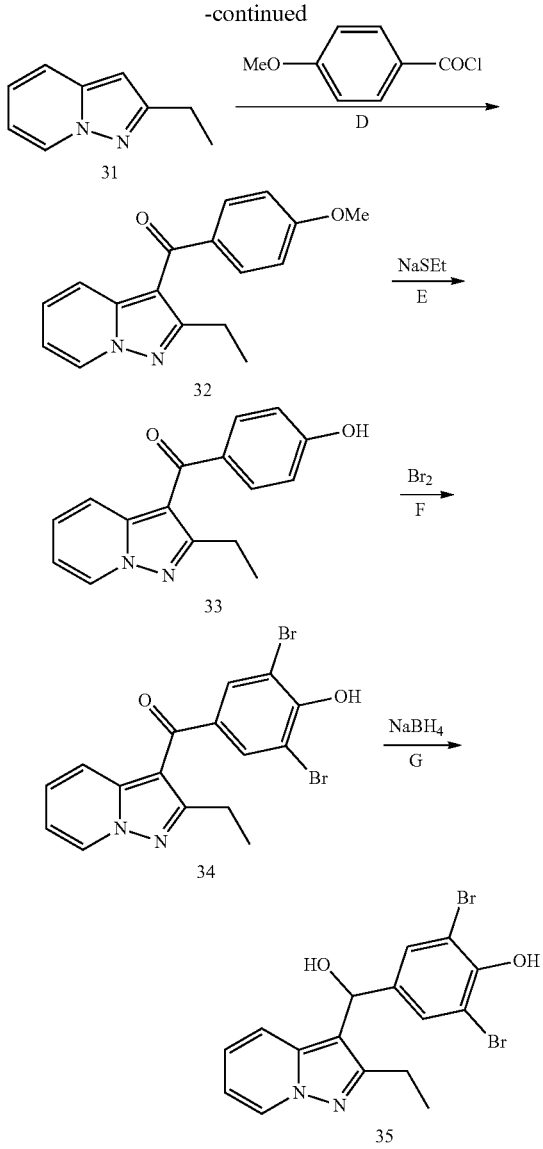

Step A: A mixture of 1-aminopyridinium iodide (15.54 g, 70.0 mmol), ethyl 2-pentynoate (9.72 g, 77.1 mmol), potassium carbonate (21.26 g, 154 mmol) and DMF (150 mL) was stirred for 4.5 h at the room temperature. The mixture was added with water (450 mL) and filtered, and the filter cake was washed with water (100 mL) to obtain ethyl 2-ethylpyrazolo[1,5-a]-pyridine-3-formate (29) (12.25 g). The compound was directly used in the next reaction without drying.

Step B: A mixture of the wet compound 29 (12.25 g), ethanol (30 mL), THF (30 mL) and 2 M sodium hydroxide aqueous solution (70 mL) was stirred overnight at 60° C. About half of the solvent was evaporated under reduced pressure, and the mixture was added with water (150 mL) and adjusted with 2 M hydrochloric acid until the pH value was 5-6. The mixture was filtered to obtain 2-ethylpyrazolo[1,5-a]pyridine-3-formic acid (30) (10.0 g). The compound was directly used in the next reaction without drying.

Step C: The wet compound 30 (5.60 g) was suspended in water (100 mL) and added with concentrated sulfuric acid (4 mL), and the obtained mixture was stirred for 3 h at 80° C. The mixture was cooled to room temperature and adjusted with 2 M sodium hydroxide aqueous solution until the pH value was 8-9. The mixture was extracted with ethyl acetate (40 mL×3), and the combined organic phase was successively washed with water (30 mL) and brine (20 mL) and dried with anhydrous sodium sulfate. The solvent was evaporated under reduced pressure to obtain 2-ethylpyrazolo[1,5-a]pyridine (31) (3.18 g). The total yield of the reactions in the steps A, B and C was 47.7%.

Step D: A mixture of the compound 31 (584 mg, 3.99 mmol), 4-methoxybenzoyl chloride (680 mg, 3.99 mmol) and aluminum trichloride (800 mg, 6.0 mmol) was stirred overnight at 100° C. The mixture was cooled slightly, added with ethyl acetate (30 mL) and water (30 mL), and adjusted with 2 M sodium hydroxide aqueous solution until the pH value was 9-10. The mixture was layered, and the organic layer was collected. The water phase was extracted with ethyl acetate (30 mL×2), and the combined organic phase was washed with brine (20 mL) and dried with anhydrous sodium sulfate. The solvent was evaporated under reduced pressure, and the product was purified by flash chromatography (200-300 meshes of silica gel, eluted with ethyl acetate:petroleum ether=1:30 to 1:10) to obtain (2-ethylpyrazolo[1,5-a]pyridine-3-yl)(4-methoxyphenyl)methanone (32) (305 mg). The yield was 27.3%. $^1$H NMR (DMSO-d6, 300 MHz) δ 8.79 (d, J=6.9 Hz, 1H), 7.66 (d, J=8.7 Hz, 2H), 7.44-7.39 (m, 1H), 7.33-7.30 (m, 1H), 7.08-7.03 (m, 3H), 3.86 (s, 3H), 2.84 (q, J=7.5 Hz, 2H), 1.21 (t, J=7.5 Hz, 3H).

Step E: 60% sodium hydride (218 mg, 5.45 mmol) was added in portions into a solution of ethanethiol (338 mg, 5.44 mmol) in DMF (3 mL), the reaction mixture was stirred for about 5 min and then added with a solution of the compound 32 (305 mg, 1.09 mmol) in DMF (3 mL), and the obtained mixture was stirred for 2 h at 120° C. The mixture was cooled to room temperature, added with water (30 mL) and adjusted with diluted hydrochloric acid until the pH value was 7-8. Subsequently, the mixture was extracted with ethyl acetate (30 mL×3), and the combined organic phase was successively washed with water (20 mL×3) and brine (20 mL) and dried with anhydrous sodium sulfate. The solvent was evaporated under reduced pressure to obtain (2-ethylpyrazolo[1,5-a]pyridine-3-yl)(4-hydroxyphenyl)methanone (33) (420 mg). The compound was directly used in the next reaction without purification. $^1$H NMR (DMSO-d6, 300 MHz) δ 10.22 (s, 1H), 8.76 (d, J=6.6 Hz, 1H), 7.56 (d, J=8.4 Hz, 2H), 7.42-7.31 (m, 2H), 7.05-7.01 (m, 1H), 6.87 (d, J=8.4 Hz, 2H), 2.84 (q, J=7.5 Hz, 2H), 1.20 (t, J=7.5 Hz, 3H). MS (EI, m/z): 265.1 $[M-H]^-$.

Step F: A solution of bromine (67 mg, 0.419 mmol) in acetic acid (1 mL) was added dropwise into a solution of the compound 33 (73 mg) and anhydrous sodium acetate (46.3 mg, 0.564 mmol) in acetic acid (5 mL), and the obtained mixture was stirred overnight at room temperature. Diluted sodium hydrogen sulfite aqueous solution was added dropwise into the reaction mixture until the color faded away. The solvent was evaporated under reduced pressure, and the reaction mixture was added with a proper amount of water and adjusted with saturated sodium bicarbonate aqueous solution until the pH value was 7-8. The mixture was extracted with ethyl acetate (40 mL×2) and dried with anhydrous sodium sulfate. The solvent was evaporated under reduced pressure, and the product was purified by flash chromatography (200-300 meshes of silica gel, eluted with ethyl acetate:petroleum ether=1:20 to 1:1) to obtain (3,5-dibromo-4-hydroxyphenyl)(2-ethylpyrazolo[1,5-a]pyridin-3-yl)methanone (34) (60 mg). The total yield of the reactions in the steps A and B was 75.4%. $^1$H NMR (DMSO-d6, 300 MHz) δ 10.77 (s, 1H), 8.81 (d, J=6.9 Hz, 1H), 7.80 (s, 2H), 7.50-7.40 (m, 2H), 7.12-7.07 (m, 1H), 2.82 (q, J=7.5 Hz, 2H), 1.23 (t, J=7.5 Hz, 3H). MS (EI, m/z): 420.9 $[M-H]^-$.

Step G: Sodium borohydride (143 mg, 3.78 mmol) was added into a mixture of the compound 34 (160 mg, 0.377 mmol), methanol (15 mL) and concentrated ammonia water (5 mL). The obtained mixture was refluxed and stirred for 0.5 h, added with sodium borohydride (143 mg, 3.78 mmol) and continuously stirred for 0.5 h, and added with sodium borohydride (143 mg, 3.78 mmol) and continuously stirred for 1 h at this temperature. The mixture was cooled to room temperature, added with water (20 mL), adjusted with 2 M citric acid aqueous solution until the pH value was 5-6, and extracted with ethyl acetate (30 mL×3). The combined organic phase was washed with brine (20 mL) and dried with anhydrous sodium sulfate. The solvent was evaporated under reduced pressure, and the product was purified by flash chromatography (200-300 meshes of silica gel, eluted with ethyl acetate:petroleum ether=1:5) to obtain 2,6-dibromo-4-[(2-ethylpyrazolo[1,5-a]pyridine-3-yl)hydroxymethyl]-phenol (35). $^1$H NMR (DMSO-d6, 400 MHz) δ 9.84 (s, 1H), 8.55-8.54 (m, 1H), 7.46-7.43 (m, 3H), 7.14-7.10 (m, 1H), 6.79-6.76 (m, 1H), 5.98 (d, J=4.0 Hz, 1H), 5.88 (d, J=4.0 Hz, 1H), 2.72 (q, J=7.6 Hz, 2H), 1.18 (t, J=7.6 Hz, 3H). MS (EI, m/z): 425.0 $[M-H]^-$.

Embodiment 10: Synthesis of 2,6-dibromo-4-[(6-bromo-2-ethylimidazo[1,2-a]-pyridine-3-yl)hydroxymethyl]phenol (40)

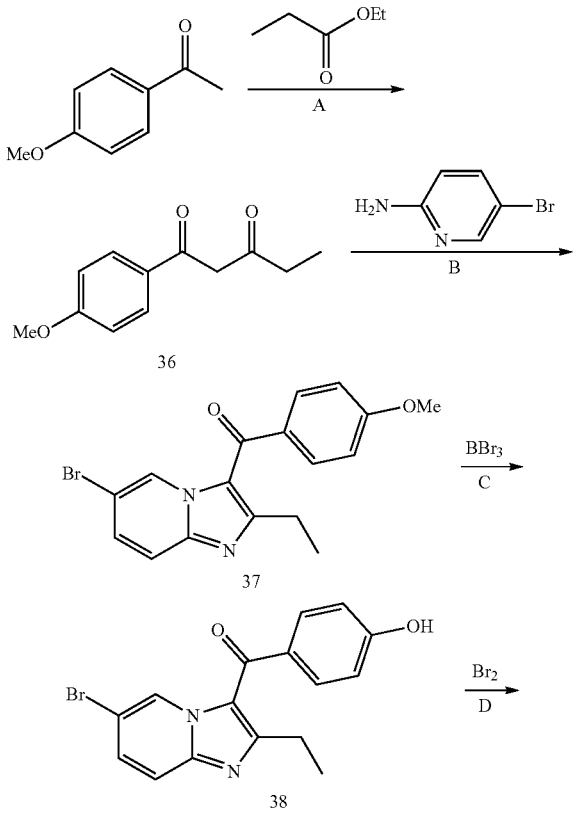

-continued

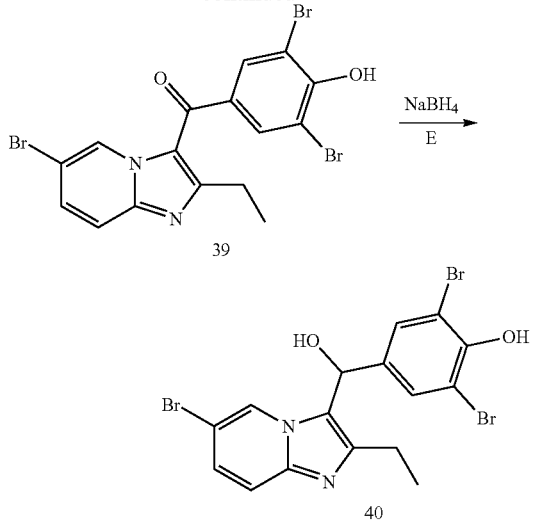

Step A: 60% sodium hydride (1.68 g, 42 mmol) was added in portions into a solution of p-methoxyacetophenone (3.0 g, 20.0 mmol) in DMF (15 mL) at −10° C. to 0° C. After addition, the mixture was continuously stirred for 40 min at this temperature and then added dropwise with ethyl propionate (2.04 g, 20 mmol). After while, the mixture was warmed to room temperature and stirred overnight. The mixture was added with water (60 mL) and extracted with ethyl acetate (30 mL×3), and the combined organic phase was washed with brine (20 mL×2) and dried with anhydrous sodium sulfate. The solvent was evaporated under reduced pressure, and the product was purified by flash chromatography (200-300 meshes of silica gel, eluted with ethyl acetate:petroleum ether=1:30) to obtain 1-(4-methoxyphenyl)pentane-1,3-dione (36) (3.16 g). The yield was 76.6%.

Step B: 2-amino-5-bromopyridine (1.3 g, 7.51 mmol) and the compound 36 (1.86 g, 9.02 mmol) were dissolved in THF (26 mL), and the mixture was successively added with iodobenzenediacetate (2.9 g, 9.00 mmol) and boron trifluoride diethyl etherate (220 mg, 1.55 mmol) in an ice-water bath, then warmed to room temperature and stirred overnight. The mixture was added with water (30 mL), adjusted with saturated sodium bicarbonate solution until the pH value was 7-8, and extracted with ethyl acetate (30 mL×3). The combined organic phase was washed with brine (20 mL) and dried with anhydrous sodium sulfate. The solvent was evaporated under reduced pressure, and the product was purified by flash chromatography (200-300 meshes of silica gel, eluted with ethyl acetate:petroleum ether=1:30) to obtain (6-bromo-2-ethylimidazo[1,2-a]pyridine-3-yl)(4-methoxyphenyl)methanone (37) (575 mg). The yield was 21.3%.

Experimental operations in steps C and D referred to the steps C and D in Embodiment 1.

Experimental operations in step E referred to the step H in Embodiment 4, and 2,6-dibromo-4-[(6-bromo-2-ethylimidazo[1,2-a]pyridine-3-yl)hydroxymethyl]phenol (40) was obtained. $^1$H NMR (DMSO-d6, 400 MHz) δ 9.98 (s, 1H), 8.40 (d, J=1.2 Hz, 1H), 7.55-7.48 (m, 1H), 7.45 (s, 2H), 7.35-7.32 (m, 1H), 6.38 (d, J=4.0 Hz, 1H), 6.26 (d, J=4.0 Hz, 1H), 2.60 (q, J=7.6 Hz, 2H), 1.18 (t, J=7.6 Hz, 3H). MS (EI, m/z): 502.9 $[M-H]^-$.

Embodiment 11: Synthesis of 2,6-dibromo-4-{[2-ethyl-7-(trifluoromethyl)-imidazo[1,2-a]pyridine-3-yl]hydroxymethyl}phenol (41)

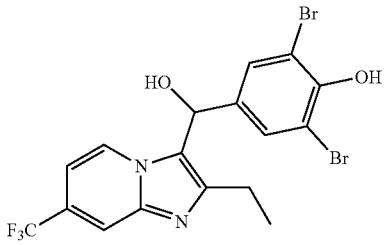

The method for preparing the compound 41 referred to Embodiment 10, wherein 2-amino-3-bromopyridine in the step B in Embodiment 10 was replaced with 2-amino-4-trifluoromethylpyridine. $^1$H NMR (DMSO-d6, 400 MHz) δ 8.39 (d, J=7.2 Hz, 1H), 8.00 (s, 1H), 7.44 (s, 2H), 7.12-7.10 (m, 1H), 6.54 (s, 1H), 6.46 (s, 1H), 6.30 (s, 1H), 2.76 (q, J=7.6 Hz, 2H), 1.25 (t, J=7.6 Hz, 3H). MS (EI, m/z): 494.9 $[M+H]^+$.

Embodiment 12: Synthesis of 2,6-dibromo-4-[(2-ethylbenzofuran-3-yl)-hydroxymethyl]phenol (42)

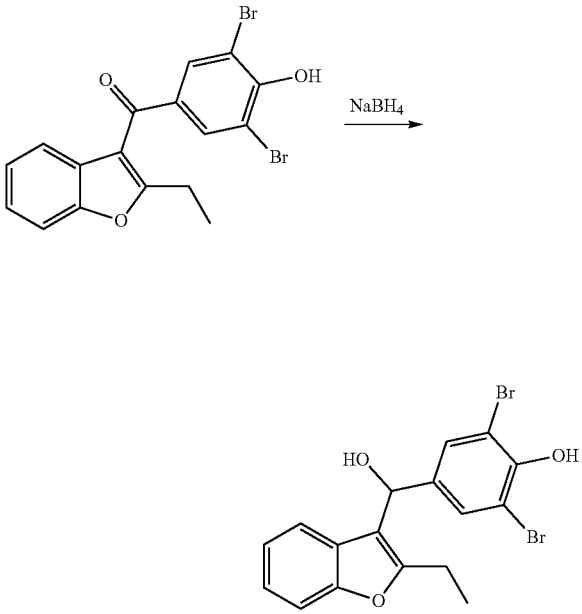

(3,5-dibromo-4-hydroxyphenyl)(2-ethylbenzofuran-3-yl) methanone was used as raw material, and the method for preparing the compound 42 referred to the step H in Embodiment 4. $^1$H NMR (DMSO-d6, 400 MHz) δ 9.87 (s, 1H), 7.53 (s, 2H), 7.48-7.46 (m, 1H), 7.40-7.38 (m, 1H), 7.22-7.18 (m, 1H), 7.14-7.11 (m, 1H), 6.03 (d, J=4.0 Hz, 1H), 5.92 (d, J=4.0 Hz, 1H), 2.90 (q, J=7.6 Hz, 2H), 1.25 (t, J=7.6 Hz, 3H). MS (EI, m/z): 425.0 $[M-H]^-$.

Embodiment 13: Synthesis of 2,6-dibromo-4-[(2-ethylimidazo[1,2-a]pyridine-3-yl)-methyl]phenol (47)

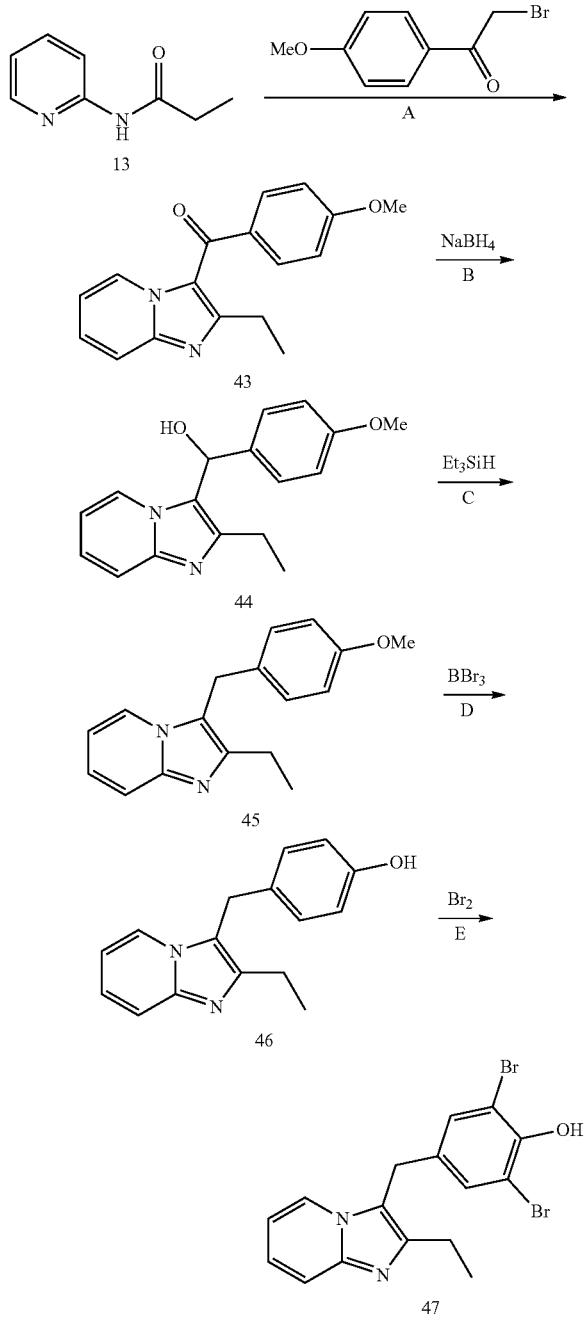

Step A: A mixture of the compound 13 (300 mg, 2.0 mmol), 2-bromo-1-(4-methoxyphenyl)ethanone (460 mg, 2.0 mmol) and methylbenzene (10 mL) was refluxed and stirred for 48 h. The mixture was cooled to room temperature, added with water (30 mL) and adjusted with saturated potassium carbonate aqueous solution until the pH value was 8-9. The mixture was extracted with ethyl acetate (40 mL×3) and dried with anhydrous sodium sulfate. The solvent was evaporated under reduced pressure, and the product was purified by flash chromatography (200 to 300 meshes of silica gel, eluted with ethyl acetate:petroleum ether=1:30 to 1:1) to obtain (2-ethylimidazo[1,2-a]pyridine-3-yl)(4-methoxyphenyl)-methanone (43) (254 mg). The yield was 45.3%. $^1$H NMR (DMSO-d6, 500 MHz) δ 9.18 (d, J=7.0 Hz, 1H), 7.74-7.69 (m, 3H), 7.58-7.55 (m, 1H), 7.17-7.14 (m, 1H), 7.09 (d, J=8.5 Hz, 2H), 3.87 (s, 3H), 2.45 (q, J=7.5 Hz, 2H), 1.11 (t, J=7.5 Hz, 3H). MS (EI, m/z): 281.1 $[M+H]^+$.

Step B: Sodium borohydride (267 mg, 7.06 mmol) was added in portions into a solution of the compound 43 (1.32 g, 4.71 mmol) in methanol (20 mL). After addition, the mixture was continuously stirred for 20 min. The mixture was added with water (100 mL), and a large amount of solid was separated out. The mixture was filtered, and the filter cake was dissolved with ethyl acetate (120 mL). The resulting solution was washed with brine (30 mL) and dried with anhydrous sodium sulfate. The solvent was evaporated under reduced pressure to obtain (2-ethylimidazo[1,2-a]pyridine-3-yl)(4-methoxyphenyl)methanone (44) (1.29 g). The yield was 97.0%. $^1$H NMR (DMSO-d6, 400 MHz) δ 8.14-8.12 (m, 1H), 7.48-7.45 (m, 1H), 7.24 (d, J=8.4 Hz, 2H), 7.16-7.12 (m, 1H), 6.90-6.88 (m, 2H), 6.74-6.72 (m, 1H), 6.23 (s, 1H), 6.07 (s, 1H), 3.72 (s, 3H), 2.74 (q, J=7.6 Hz, 2H), 1.26 (t, J=7.6 Hz, 3H).

Step C: Triethylsilicane (1.31 g, 11.3 mmol) was added into a solution of the compound 44 (1.06 g, 3.75 mmol) and boron trifluoride diethyl etherate (2.66 g, 18.7 mmol) in dichloromethane (40 mL), and the obtained mixture was stirred for 3 h at room temperature. The mixture was added with water (40 mL) and adjusted with saturated sodium bicarbonate solution until the pH value was 7-8. The mixture was layered, the water phase was extracted with dichloromethane (40 mL×2), and the combined organic phase was washed with brine (30 mL) and dried with anhydrous sodium sulfate. The solvent was evaporated under reduced pressure, and the product was recrystallized with dichloromethane/petroleum ether to obtain 2-ethyl-3-(4-methoxybenzyl)imidazo[1,2-a]pyridine (45) (896 mg). The yield was 89.7%.

Experimental operations in steps D and E referred to the steps C and D in Embodiment 1 to obtain 2,6-dibromo-4-[(2-ethylimidazo[1,2-a]pyridine-3-yl)methyl]phenol (47). $^1$H NMR (DMSO-d6, 400 MHz) δ 9.84 (s, 1H), 8.15 (d, J=6.8 Hz, 1H), 7.49 (d, J=8.8 Hz, 1H), 7.29 (s, 2H), 7.20-7.16 (m, 1H), 6.86-6.83 (m, 1H), 4.25 (s, 2H), 2.75 (q, J=7.6 Hz, 2H), 1.25 (t, J=7.6 Hz, 3H). MS (EI, m/z): 409.0 $[M-H]^-$.

Embodiment 14: Synthesis of (3,5-dibromo-4-hydroxyphenyl)(6-ethylimidazo-[2,1-b][1,3,4]thiadiazole-5-yl)methanone (49)

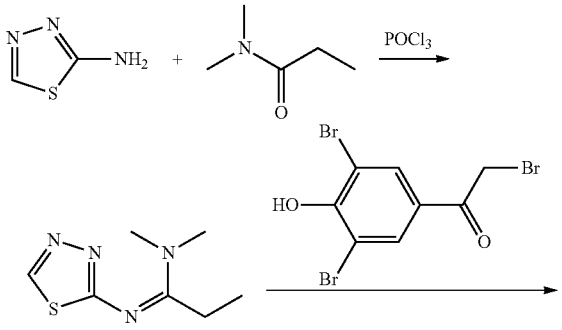

-continued

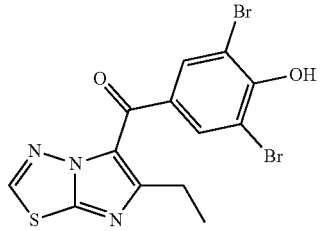

The method for preparing the compound 49 referred to the steps A and B in Embodiment 2, wherein 2-aminothiazole in the step A in Embodiment 2 was replaced with 2-amino-1,3,4-thiadiazole and 2-bromo-1(4-methoxyphenyl)ethanone was replaced with 2-bromo-1-(3,5-dibromo-4-methoxyphenyl)ethanone. $^1$H NMR (DMSO-d6, 400 MHz) δ 9.23 (s, 1H), 7.84 (s, 2H), 2.69 (q, J=7.6 Hz, 2H), 1.22 (t, J=7.6 Hz, 3H). MS (EI, m/z): 429.8 $[M-H]^-$.

Embodiment 15: Synthesis of 2-bromo-4-(2-ethylimidazo[1,2-a]pyridine-3-yl)-hydroxymethyl-6-methylphenol (54)

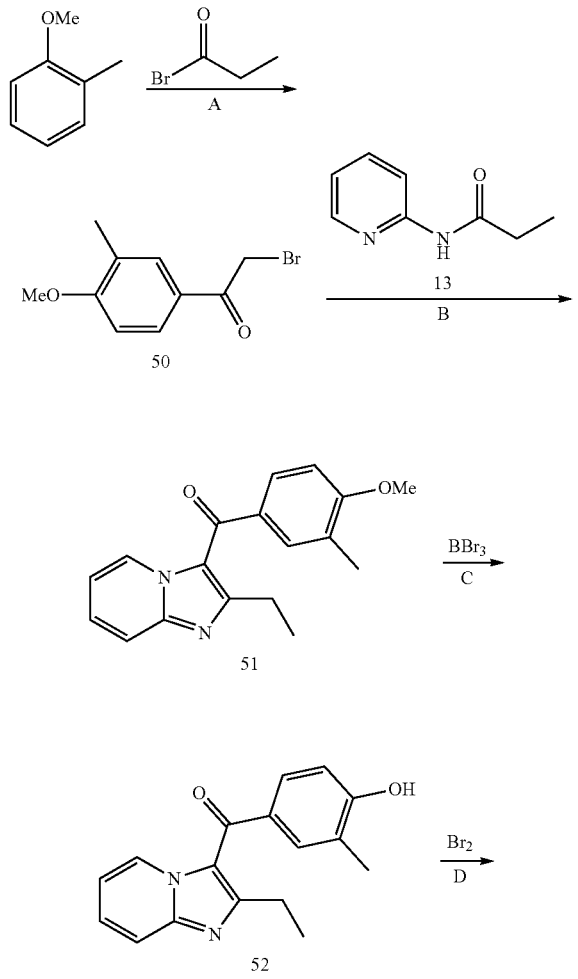

-continued

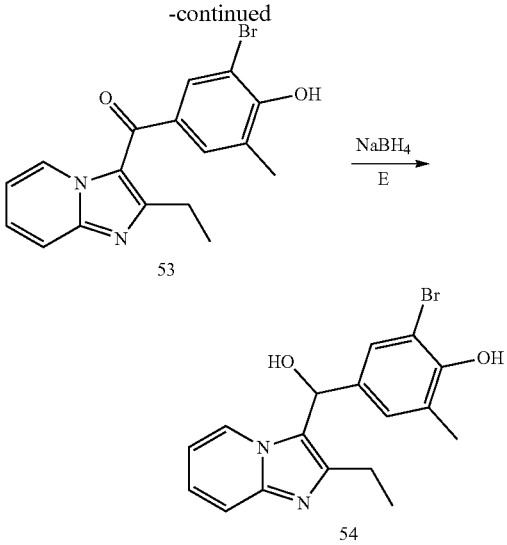

Step A: A solution of bromoacetyl bromide (9.9 g, 49.0 mmol) in dichloromethane (10 mL) was added dropwise into a solution of 2-methylanisole (5.0 g, 40.9 mmol) and aluminum trichloride (6.0 g, 45.0 mmol) in dichloromethane (40 mL) for about 20 min at 0° C. to 5° C. After addition, the obtained mixture was continuously stirred for 2.0 h at this temperature. The reaction solution was poured into a proper amount of ice water in batches and extracted with dichloromethane (60 mL×3). The combined organic phase was successively washed with water (30 mL), saturated sodium bicarbonate aqueous solution (30 mL×2), water (30 mL) and brine (30 mL) and then dried with anhydrous sodium sulfate. The organic phase was filtered by a short silica gel column. The solvent was evaporated under reduced pressure, and the product was purified by flash chromatography (200-300 meshes of silica gel, eluted with ethyl acetate:petroleum ether=1:100 to 1:30) to obtain 2-bromo-1-(3-methyl-4-methoxyphenyl)ethanone (50) (3.0 g). The yield was 30.2%.

Step B: A mixture of the compound 13 (1.85 g, 12.3 mmol), the compound 50 (3.0 g, 12.3 mmol) and methylbenzene (30 mL) was refluxed and stirred overnight. The mixture was cooled to—room temperature, added with water (50 mL) and adjusted with 2 M potassium carbonate aqueous solution until the pH value was 8-9. The mixture was extracted with dichloromethane (60 mL×3) and dried with anhydrous sodium sulfate. The product was purified by flash chromatography (200 to 300 meshes of silica gel, eluted with ethyl acetate:petroleum ether=1:10 to 1:5) to obtain (3-methyl-4-methoxyphenyl)(2-ethylimidazo[1,2-a]pyridine-3-yl)-methanone (51) (1.7 g). The yield was 47.0%.

Step C: A solution of 1.0 M boron tribromide in methylbenzene (6.8 mL) was added dropwise into a solution of the compound 51 (800 mg, 2.72 mmol) in anhydrous dichloromethane (20 mL) in an ice-water bath, and the obtained mixture was stirred for 6 h in the ice-water bath. The reaction mixture was poured into a proper amount of ice water and adjusted with saturated sodium bicarbonate aqueous solution until the pH value was 7-8. The mixture was extracted with ethyl acetate (40 mL×2) and dried with anhydrous sodium sulfate. The solvent was evaporated under reduced pressure, and the product was purified by flash chromatography (200-300 meshes of silica gel, eluted with ethyl acetate:petroleum ether=1:5 to 2:1) to obtain (3-methyl-4-hydroxyphenyl)(2-ethylimidazo[1,2-a]pyridine-3-yl)methanone (52) (630 mg). The yield was 82.6%.

Step D: NBS (440 mg, 2.47 mmol) was added in portions into a solution of the compound 52 (630 mg, 2.25 mmol) in DMF (10 mL), and the obtained mixture was stirred for 1 h at room temperature. The mixture was added with water (40 mL), extracted with ethyl acetate (30 mL×3) and dried with anhydrous sodium sulfate. The solvent was evaporated under reduced pressure, and the product was purified by flash chromatography (200-300 meshes of silica gel, eluted with ethyl acetate:petroleum ether=1:3 to 1:1) to obtain (3-bromo-4-hydroxy-5-methylphenyl)-(2-ethylimidazo[1,2-a]pyridine-3-yl)methanone (53) (625 mg). The yield was 77.3%.

Experimental operations in step E referred to the step H in Embodiment 4 to obtain 2-bromo-4-(2-ethylimidazo[1,2-a]pyridine-3-yl)hydroxymethyl-6-methylphenol (54). $^1$H NMR (DMSO-d6, 400 MHz) δ 9.07 (s, 1H), 8.04 (d, J=6.8 Hz, 1H), 7.50 (d, J=8.8 Hz, 1H), 7.26-7.17 (m, 2H), 6.97 (s, 1H), 6.80-6.77 (m, 1H), 5.86 (s, 1H), 2.77 (q, J=7.6 Hz, 2H), 2.16 (s, 3H), 1.25 (t, J=7.6 Hz, 3H). MS (EI, m/z): 360.0 $[M-H]^-$.

Embodiment 16: Synthesis of 2,6-dibromo-4-[(2-ethylbenzofuran-3-yl)(methoxy)-methyl]phenol (58)

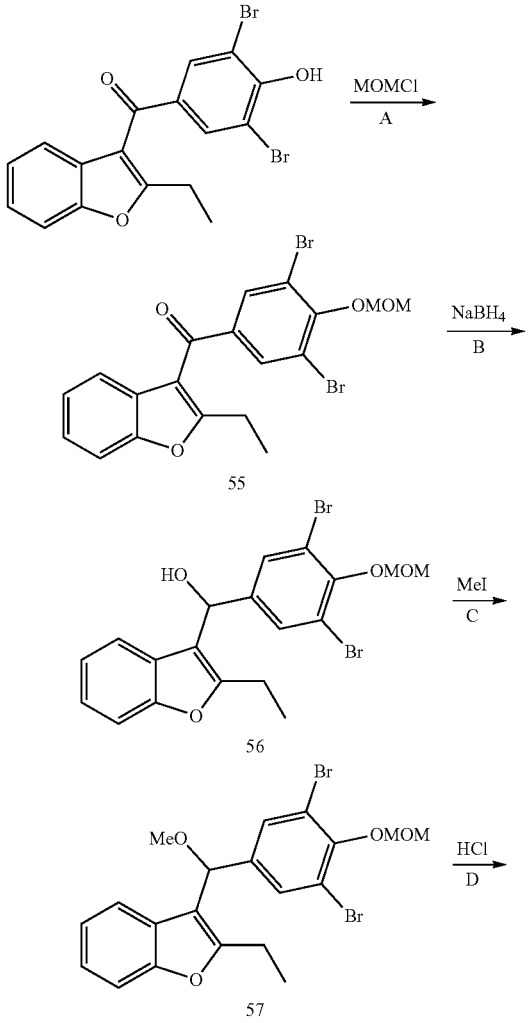

-continued

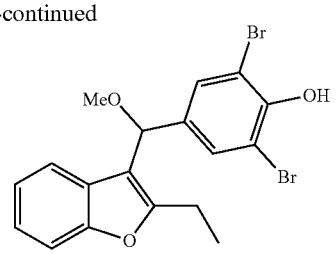

58

Step A: A mixture of benzbromarone (100 mg, 0.236 mmol), diisopropylethylamine (46 mg, 0.356 mmol), chloromethylmethylether (28 mg, 0.348 mmol) and dichloromethane (6 mL) was stirred overnight at room temperature. The mixture was added with water (20 mL) and extracted with ethyl acetate (15 mL×3), and the combined organic phase was successively washed with water (10 mL) and brine (10 mL), and then dried with anhydrous sodium sulfate. The solvent was evaporated under reduced pressure to obtain [3,5-dibromo-4-(methoxymethoxy)phenyl](2-ethylbenzofuran-3-yl)methanone (55) (108 mg). The yield was 97.8%.

Step B: Sodium borohydride (87 mg, 2.30 mmol) was added into a solution of the compound 55 (108 mg, 0.230 mmol) in methanol (15 mL) at the room temperature. After addition, the obtained mixture was stirred for 1.5 h at 40° C. Most of the solvent was evaporated under reduced pressure, the mixture was added with water (20 mL) and extracted with ethyl acetate (20 mL×2), and the combined organic phase was successively washed with water (15 mL) and brine (10 mL) and dried with anhydrous sodium sulfate. The solvent was evaporated under reduced pressure to obtain [3,5-dibromo-4-(methoxymethoxy)phenyl](2-ethylbenzofuran-3-yl)methanol (56) (105 mg). The yield was 97.0%.

Step C: 60% sodium hydride (13 mg, 0.325 mmol) was added into a solution of the compound 56 (100 mg, 0.213 mmol) in DMF (5 mL) in an ice-water bath. The mixture was continuously stirred for 30 min and then added with iodomethane (60 mg, 0.422 mmol), and the obtained mixture was stirred overnight at room temperature. The mixture was added with water (15 mL) and extracted with ethyl acetate (15 mL×2), and the combined organic phase was successively washed with water (10 mL) and brine (10 mL) and dried with anhydrous sodium sulfate. The solvent was evaporated under reduced pressure to obtain 3-{[3,5-dibromo-4-(methoxymethoxy)phenyl](methoxy)methyl}-2-ethylbenzofuran (57) (102 mg). The yield was 98.9%.

Step D: Concentrated hydrochloric acid (3 mL) was added into a solution of the compound 57 (100 mg, 0.207 mmol) in methanol (3 mL), and the obtained mixture was stirred for 1 h at room temperature. The mixture was added with water (20 mL) and extracted with ethyl acetate (15 mL×2), and the combined organic phase was successively washed with water (10 mL) and brine (10 mL) and dried with anhydrous sodium sulfate. The solvent was evaporated under reduced pressure, and the product was purified by flash chromatography (200-300 meshes of silica gel, eluted with ethyl acetate:petroleum ether=1:60) to obtain 2,6-dibromo-4-[(2-ethylbenzofuran-3-yl)(methoxy)methyl]phenol (58). $^1$H NMR (DMSO-d6, 400 MHz) δ 9.93 (s, 1H), 7.51-7.49 (m, 3H), 7.40-7.38 (m, 1H), 7.24-7.20 (m, 1H), 7.16-7.13 (m, 1H), 5.60 (s, 1H), 3.28 (s, 3H), 2.92 (q, J=7.6 Hz, 2H), 1.25 (t, J=7.6 Hz, 3H). MS (EI, m/z): 439.0 $[M-H]^-$.

Embodiment 17: Synthesis of 2,6-dibromo-4-{(2-ethyl-7-methoxyimidazo[1,2-a]-pyridine-3-yl) hydroxymethyl}phenol (64)

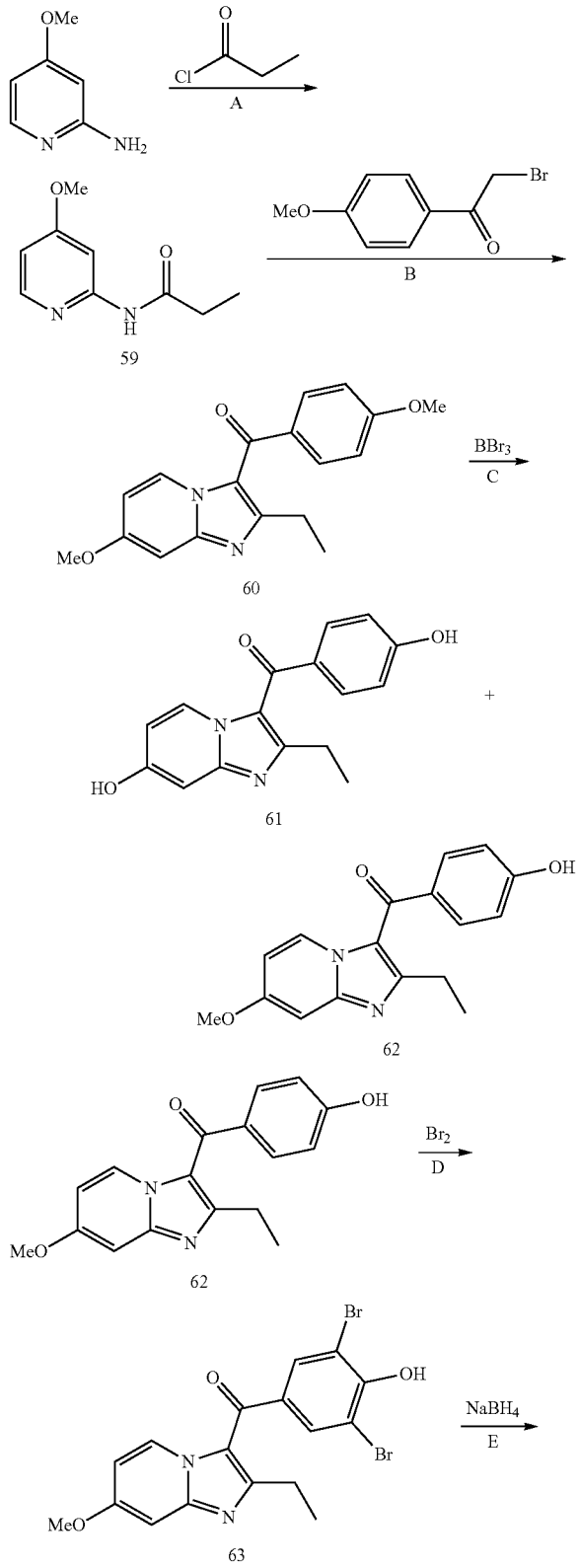

-continued

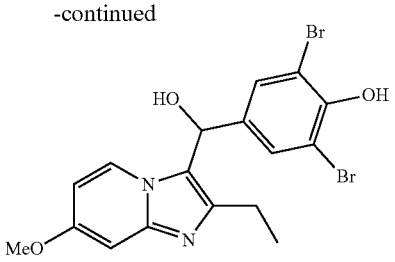

64

Step A: 2-amino-4-methoxypyridine (4.9 g, 39.5 mmol) and triethylamine (4.4 g, 43.5 mmol) were dissolved in tetrahydrofuran (30 mL) and added dropwise with propionyl chloride (4.0 g, 43.5 mmol) in an ice-water bath, and the obtained mixture was stirred overnight at room temperature. The mixture was added with water (100 mL) and extracted with ethyl acetate (60 mL×3), the combined organic phase was washed with brine (30 mL), and the solvent was evaporated under reduced pressure. Potassium carbonate (4.1 g, 29.7 mmol), methanol (50 mL) and water (12 mL) were added into the product, and the obtained mixture was stirred for 1 h at room temperature. The solvent was evaporated under reduced pressure, the mixture was added with water (20 mL) and extracted with ethyl acetate (30 mL×3), and the combined organic phase was washed with brine (15 mL) and dried with anhydrous sodium sulfate. The solvent was evaporated under reduced pressure to obtain N-(4-methoxypyridine-2-yl)-propionamide (59) (4.85 g). The yield was 68.2%.

Step B: A mixture of the compound 59 (4.85 g, 26.9 mmol), 2-bromo-1-(4-methoxyphenyl)ethanone (6.14 g, 26.9 mmol) and methylbenzene (50 mL) was refluxed and stirred overnight. The mixture was cooled to the room temperature, added with water (50 mL) and adjusted with 2 M potassium carbonate solution until the pH value was 8-9. The mixture was extracted with dichloromethane (70 mL×3) and dried with anhydrous sodium sulfate. The solvent was evaporated under reduced pressure, and the product was purified by flash chromatography (200-300 meshes of silica gel, eluted with ethyl acetate:petroleum ether=1:5 to 2:3) to obtain (2-ethyl-7-methoxyimidazo[1,2-a]pyridine-3-yl)(4-methoxyphenyl)methanone (60) (900 mg). The yield was 10.8%. $^1$H NMR (DMSO-d6, 400 MHz) δ 9.08 (d, J=7.6 Hz, 1H), 7.67 (d, J=8.8 Hz, 2H), 7.17 (s, 1H), 7.08 (d, J=8.4 Hz, 2H), 6.88-6.86 (m, 1H), 3.91 (s, 3H), 3.87 (s, 3H), 2.38 (q, J=7.2 Hz, 2H), 1.10 (t, J=7.2 Hz, 3H).

Step C: A solution of 1.0 M boron tribromide in methylbenzene (9 mL) was added dropwise into a solution of the compound 60 (900 mg, 2.9 mmol) in anhydrous dichloromethane (25 mL) in an ice-water bath, and the obtained mixture was stirred overnight at—room temperature. The reaction solution was poured into ice water (50 mL) and adjusted with saturated sodium bicarbonate aqueous solution until the pH value was 7-8. The mixture was extracted with ethyl acetate (40 mL×3) and dried with anhydrous sodium sulfate. The solvent was evaporated under reduced pressure, and the product was purified by flash chromatography (200-300 meshes of silica gel, eluted with methanol: dichloromethane=1:50 to 1:20) to obtain (2-ethyl-7-hydroxyimidazo[1,2-a]pyridine-3-yl)(4-hydroxyphenyl) methanone (61) (477 mg) and (2-ethyl-7-methoxyimidazo[1,2-a]pyridine-3-yl)(4-hydroxyphenyl)-methanone (62) (277 mg). The yields were 58.3% and 32.2% respectively. Compound 61: $^1$H NMR (DMSO-d6, 400 MHz) δ 10.83 (s, 1H), 10.22 (s, 1H), 9.06 (d, J=7.6 Hz, 1H), 7.54 (d, J=8.4 Hz, 2H), 6.89-6.84 (m, 3H), 6.77-6.75 (m, 1H), 2.37 (q, J=7.6 Hz, 2H), 1.08 (t, J=7.6 Hz, 3H). Compound 62: $^1$H NMR (DMSO-d6, 400 MHz) δ 10.25 (s, 1H), 9.03 (d, J=7.6 Hz, 1H), 7.57 (dd, J=2.0, 6.8 Hz, 2H), 7.15 (d, J=2.4 Hz, 1H), 6.91-6.83 (m, 3H), 3.91 (s, 3H), 2.45 (q, J=7.6 Hz, 2H), 1.11 (t, J=7.6 Hz, 3H).

Experimental operations in steps D and E referred to the steps F and G in Embodiment 9 to obtain 2,6-dibromo-4-{(2-ethyl-7-methoxyimidazo[1,2-a]pyridine-3-yl) hydroxymethyl}phenol (64). $^1$H NMR (DMSO-d6, 400 MHz) δ 7.95 (d, J=7.6 Hz, 1H), 7.40 (s, 2H), 6.87 (s, 1H), 6.52 (d, J=7.6 Hz, 1H), 6.25 (d, J=3.6 Hz, 1H), 6.14 (d, J=3.6 Hz, 1H), 3.79 (s, 3H), 2.63 (q, J=7.6 Hz, 2H), 1.22 (t, J=7.6 Hz, 3H). MS (EI, m/z): 453.0 [M−H]$^-$.

Embodiment 18: Synthesis of (3,5-dibromo-4-hydroxyphenyl)(2-propylfurano[2,3-b]-pyridine-3-yl) methanone (69)

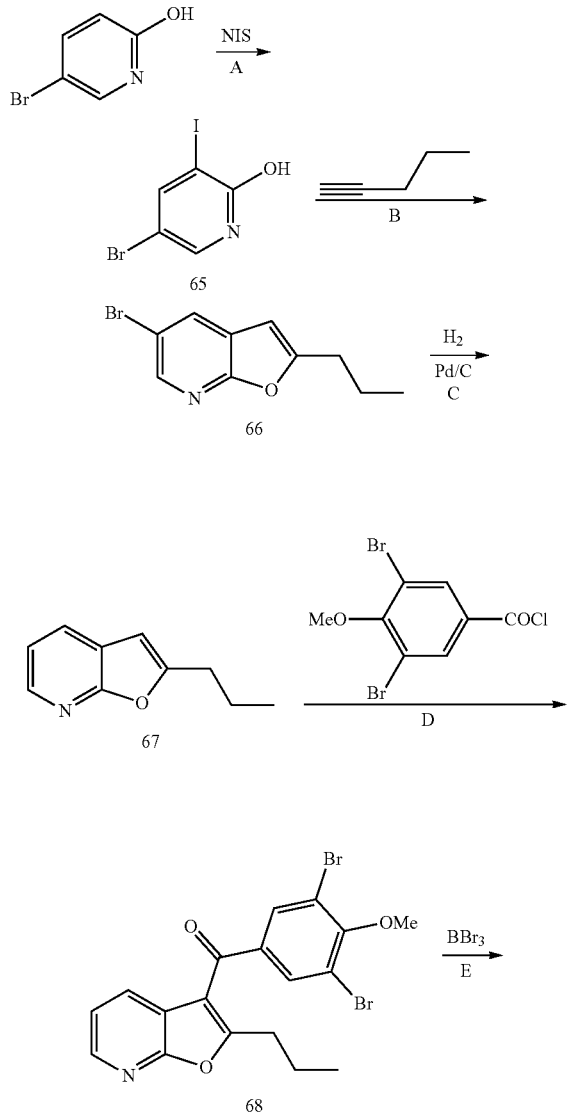

-continued

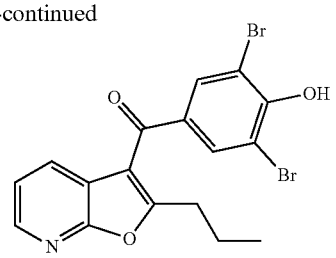

69

Step A: A mixture of 5-bromo-2-hydroxypyridine (2.5 g, 14.4 mmol), iodosuccinimide (4.7 g, 20.9 mmol) and acetonitrile (40 mL) is stirred for 20 min at 82° C. The mixture was cooled to room temperature and then filtered, and the filter cake was recrystallized with ethyl acetate to obtain 5-bromo-2-hydroxy-3-iodopyridine (65) (4.0 g). The yield was 92.6%.

Step B: 1-pentyne (1.09 g, 16.0 mmol) was added into a mixture of the compound 65 (4.0 g, 13.3 mmol), cuprous iodide (254 mg, 1.33 mmol), bis(triphenylphosphine)palladium dichloride (468 mg, 0.667 mmol) and triethylamine (50 mL), and the obtained mixture was stirred overnight at 50° C. The solvent was evaporated under reduced pressure, the mixture was added with water (80 mL) and extracted with ethyl acetate (50 mL×3), and the combined organic phase was washed with brine (30 mL) and dried with anhydrous sodium sulfate. The solvent was evaporated under reduced pressure. The product was purified by flash chromatography (200-300 meshes of silica gel, eluted with ethyl acetate:petroleum ether=1:200 to 1:100) to obtain 5-bromo-2-propylfurano[2,3-b]pyridine (66) (1.72 g). The yield was 53.9%. $^1$H NMR (DMSO-d6, 400 MHz) δ 8.29-8.25 (m, 2H), 6.67 (s, 1H), 2.80-2.78 (m, 2H), 1.73-1.71 (m, 2H), 0.96 (t, J=7.2 Hz, 3H).

Step C: The compound 66 (1.0 g, 4.16 mmol) was dissolved in methanol (20 mL) and added with 10% palladium carbon (100 mg), and the obtained mixture was hydrogenated in the atmosphere of hydrogen at 40° C. under the normal pressure. The mixture was filtered by kieselguhr, and the solvent was evaporated under reduced pressure to obtain 2-propylfurano[2,3-b]pyridine (67) (620 mg). The yield was 92.5%. $^1$H NMR (DMSO-d6, 400 MHz) δ 8.20-8.18 (m, 1H), 8.00-7.98 (m, 1H), 7.30-7.27 (m, 1H), 6.67 (s, 1H), 2.80-2.76 (m, 2H), 1.76-1.70 (m, 2H), 0.97 (t, J=7.6 Hz, 3H).

Step D: A mixture of the compound 67 (50 mg, 0.31 mmol), 3,5-dibromo-4-methoxybenzoyl chloride (280 mg, 0.853 mmol) and diisopropylethylamine (5 mL) was stirred overnight at 110° C. The solvent was evaporated under reduced pressure, and the mixture was added with water (30 mL) and extracted with ethyl acetate (30 mL×3). The combined organic phase was washed with brine (15 mL) and dried with anhydrous sodium sulfate, and the solvent was evaporated under reduced pressure. The product was purified by flash chromatography (200-300 meshes of silica gel, eluted with ethyl acetate:petroleum ether=1:50 to 1:8) to obtain (3,5-dibromo-4-methoxyphenyl)(2-propylfuro[2,3-b]pyridin-3-yl)-methanone (68) (54 mg). The yield was 38.4%. $^1$H NMR (DMSO-d6, 400 MHz) δ 8.16 (s, 2H), 7.84-7.81 (m, 1H), 7.70 (s, 1H), 6.13-6.10 (m, 1H), 3.84 (s, 3H), 2.95-2.90 (m, 2H), 2.01-1.95 (m, 2H), 1.23-1.20 (m, 3H).

Experimental operations in step E referred to the step B in Embodiment 15 to obtain (3,5-dibromo-4-hydroxyphenyl)(2-propylfuro[2,3-b]pyridine-3-yl)methanone(69). MS (EI, m/z): 440.1 $[M+H]^+$.

Embodiment 19: Inhibition Assay of Uric Acid Transport for Compounds in HEK293-hURAT1 Transfection Cell Line I. Materials The HEK293 cell line was purchased from Cell Resource Center of Shanghai Institutes for Biological Sciences of the Chinese Academy of Sciences. The plasmid pCMV6-hURAT1 was purchased from Origene Technologies, Inc. Geneticin (G418) was purchased from Sangon Biotech Co., Ltd. Poly-lysine was purchased from Sigma-Aldrich Co. LLC. $^{14}$C-uric acid was purchased from American Radiolabeled Chemicals, Inc. Sodium gluconate, potassium gluconate, calcium gluconate, $KH_2PO_4$, $MgSO_4$, glucose and HEPES were purchased from Sinopharm Chemical Reagent Co., Ltd. DMEM culture medium and fetal bovine serum were purchased from Thermo Fisher Scientific Inc. Benzbromarone was purchased from Sigma-Aldrich Co. LLC.

II. Experimental Methods

1. Construction of a HEK293 Cell Line with High Expression of hURAT1:

The plasmid pCMV6-hURAT1 was transfected into HEK293 cells, and then the stable strain was obtained by the G418 (final concentration of 500 μg/mL) resistance screening, which is the high expression of hURAT1 transporter membrane protein. It can be used for in vitro inhibition assay of uric acid transporter hURAT1 (Weaver Y M, Ehresman D J, Butenhoff J L, et al. Roles of rat renal organic anion transporters in transporting perfluorinated carboxylates with different chain lengths. Toxicological Sciences, 2009, 113 (2):305-314). The HEK293 cells are the human embryonic kidney cells with high transfection efficiency, and are a very commonly used engineering cell line for expressing exogenous genes.

2. To a coated 24-well plate was added 200 μl of 0.1 mg/mL poly-lysine per well and the plate was left overnight. Poly-lysine was removed from wells. The wells were cleaned thoroughly with sterile water and dried for use.

3. To the above coated 24-well plate was added HEK293-hURAT1 stable cells ($2\times10^5$ cells per well). The cells were cultured at 37° C. under 5% $CO_2$ for 3 days.

4. Preparation of an HBSS buffer: weighted following reagents according to the final concentration of 125 mM sodium gluconate, 4.8 mM potassium gluconate, 1.3 mM calcium gluconate, 1.2 mM $KH_2PO_4$, 1.2 mM $MgSO_4$, 5.6 mM glucose and 25 mM HEPES with deionized water. The solution was fully mixed to give HBSS (pH value: 7.4). The buffer was stored at −20° C.

5. The HBSS buffer was warmed to 37° C. in a water bath. Taken out the 24-well plate with HEK293-hURAT1 stable cells, removed the culture medium and washed cells with HBSS, then added 160 μL of HBSS and 20 μL test compound per well. The final concentration of tested compound per well is 500 nM. The blank control well contains only 180 μL of HBSS without tested compound. The plate was placed at room temperature for 10 min.

6. To each well was added 20 μL of 50 μM $^{14}$C-Uric acid. The 24-well plate was placed at room temperature for 20 min.

7. The solution in each well was removed and the cells were washed with the pre-cooled HBSS buffer. To each well was added 0.2 M NaOH to dissolve the cells. The solution containing cell fragments was collected and the right amount of scintillation liquid was added. The radioisotope intensity of the $^{14}C$-Uric acid (CPM value) was then detected by using PerkinElmer MicroBeta Trilux 1450 liquid scintillation analyzer.

8. The formula for calculating the inhibitory rate of uric acid transport for compounds was shown as below (Table 1), the CPM value of the tested compounds was represented by $CPM_{(tested\ compound)}$ and the CPM value of the blank control was represented by $CPM_{(blank\ control)}$. All tests were repeated three times, and the results were averaged and the standard deviation (SD) was calculated:

$$\text{Inhibitory rates } (\%)_{(500\ nM\ compound\ concentration)} = (CPM_{(blank\ control)} - CPM_{(tested\ compound)})/CPM_{(blank\ control)} \times 100\%$$

III. Experimental Results

The results showed that in comparison with the control drug benzbromarone at the concentration of 500 nM, the compounds 8, 12, 20, 23 and 40 have very good inhibitory effects of uric acid transport in HEK293-hURAT1 transfection cell line.

TABLE 1

Inhibitory rates of uric acid transport for test compounds\and benzbromarone at 500 nM in HEK293-hURAT1 transfection cell line

| Compound number or drug | Inhibitory rates of uric acid transport, ±SD (%) |
|---|---|
| Benzbromarone | 54.77 ± 5.12 |
| 4 | 49.98 ± 5.38 |
| 8 | 55.23 ± 3.94 |
| 12 | 51.31 ± 0.16 |
| 20 | 62.10 ± 1.26 |
| 21 | 32.95 ± 7.33 |
| 22 | 48.16 ± 3.86 |
| 23 | 50.16 ± 1.02 |
| 28 | 41.18 ± 1.92 |
| 35 | 36.26 ± 1.79 |
| 40 | 51.70 ± 2.43 |
| 41 | 37.36 ± 5.52 |
| 42 | 37.40 ± 2.36 |
| 49 | 31.91 ± 0.23 |
| 54 | 42.89 ± 3.44 |
| 58 | 48.68 ± 5.61 |
| 64 | 39.94 ± 5.34 |

What is claimed is:

1. A compound or pharmaceutically acceptable salt thereof[for treating and preventing a metabolic disease in uric acid excretion], wherein the compound is selected from the group consisting of:

(3,5-dibromo-4-hydroxyphenyl)(2-ethylimidazo[1,2-a]pyrimidine-3-yl)methanone;

(3,5-dibromo-4-hydroxyphenyl)(2-ethylimidazo[2,1-b]thiozole-5-yl)methanone;

(3,5-dibromo-4-hydroxyphenyl)(2-ethylimidazo[1,2-a]pyrazine-3-yl)methanone;

3-bromo-5-[(2-ethylimidazo[1,2-a]pyridine-3-yl)hydroxymethyl]-2-hydroxybenzonitrile;

5-[(2-ethylimidazo[1,2-a]pyridine-3-yl)hydroxymethyl]-2-hydroxybenzonitrile;

2,6-dibromo-4-[(6-ethylimidazo[2,1-b]thiozole-5-yl)hydroxymethyl]phenol;

2,6-dibromo-4-[(2-ethylimidazo[1,2-a]pyrazine-3-yl)hydroxymethyl]phenol;

2-bromo-4-[(2-ethyl-6-fluoroimidazo[1,2-a]pyridine-3-yl)hydroxymethyl]-6-fluorophenol;

2,6-dibromo-4-[(2-ethylpyrazolo[1,5-a]pyridine-3-yl)hydroxymethyl]phenol;

2,6-dibromo-4-[(6-bromo-2-ethylimidazo[1,2-a]pyridine-3-yl)hydroxymethyl]phenol;

2,6-dibromo-4-{[(2-ethyl-7-(trifluoromethyl)imidazo[1,2-a]pyridine-3-yl)]hydroxymethyl}phenol;

2,6-dibromo-4-[(2-ethylimidazo[1,2-a]pyridine-3-yl)methyl]phenol;

(3,5-dibromo-4-hydroxyphenyl)(6-ethylimidazo[2,1-b][1,3,4]thiodiazole-5-yl)methanone;

2-bromo-4-(2-ethylimidazo[1,2-a]pyridine-3-yl)hydroxymethyl-6-methylphenol;

2,6-dibromo-4-{(2-ethyl-7-methoxyimidazo[1,2-a]pyridine-3-yl)hydroxymethyl}phenol;

(3,5-dibromo-4-hydroxyphenyl)(2-propylfuro[2,3-b]pyridine-3-yl)methanone.

2. A pharmaceutical acceptable composition comprising the compound of claim 1 or its pharmaceutically acceptable salt as active ingredient, and a pharmaceutically acceptable carrier.

3. A method for treating and preventing a metabolic disease in uric acid excretion comprising a step of administrating to a subject in need a therapeutically effective amount of the compound of claim 1 or its pharmaceutically acceptable salt; wherein the metabolic disease in uric acid excretion is hyperuricemia or gout.

*4. A compound selected from the group consisting of:*

(II-A)

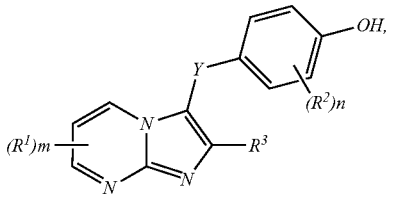

(II-B)

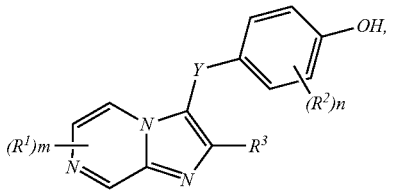

(II-C)

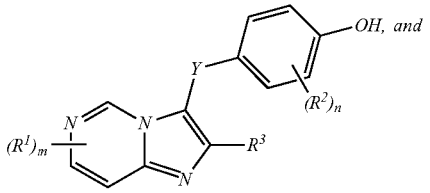

(V-B)

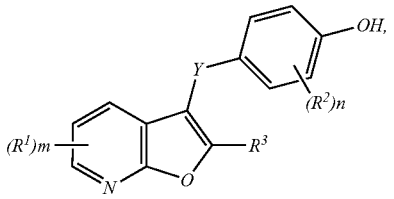

*or a pharmaceutically acceptable salt thereof, wherein:*

*the*

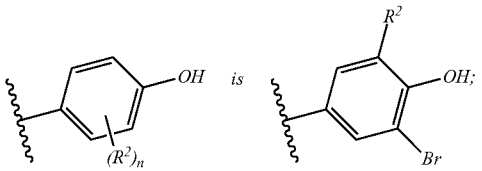

*Y is carbonyl, sulfur, sulfone, sulfoxide, optionally substituted methylene, or imino, provided that when D is N such that the ring A forms a pyridine ring, Y is not a carbonyl group;*

*each $R^1$ is independently selected from the group consisting of hydrogen, deuterium, hydroxy, halogen, nitro, amino, cyano, $C_{1-3}$ alkyl, substituted $C_{1-3}$ alkyl, substituted $C_{1-3}$ amino, $C_{1-3}$ alkoxy, and substituted $C_{1-3}$ alkoxy;*

*$R^2$ is selected from the group consisting of hydroxy, halogen, nitro, amino, cyano, $C_{1-3}$ alkyl, substituted $C_{1-3}$ alkyl, and substituted $C_{1-3}$ amino;*

*$R^3$ is selected from the group consisting of $C_{1-4}$ alkyl, substituted $C_{1-4}$ alkyl, and halogen;*

*m is an integer from 0 to 3;*

*n is an integer from 1 to 3; and*

*the substituent in the group $R^1$, $R^2$ or $R^3$ is each independently selected from the group consisting of hydroxyl, halogen, nitro, amino, and cyano.*

*5. The compound of claim 4, wherein Y is carbonyl.*

*6. The compound of claim 4, wherein each $R^1$ is independently selected from the group consisting of hydrogen, halogen, and $C_{1-3}$ alkyl substituted with halogen.*

*7. The compound of claim 4, wherein $R^2$ is selected from the group consisting of halogen, cyano, and $C_{1-3}$ alkyl substituted with halogen.*

*8. The compound of claim 4, wherein $R^3$ is ethyl or propyl.*

*9. The compound of claim 4, wherein m is 1.*

*10. The compound of claim 4, wherein $R^1$ is —H.*

*11. The compound of claim 4, having Formula II-A:*

*(II-A)*

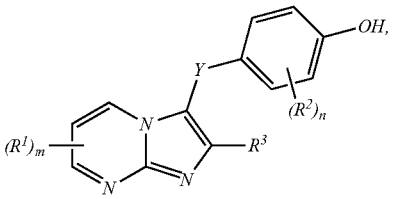

*wherein the*

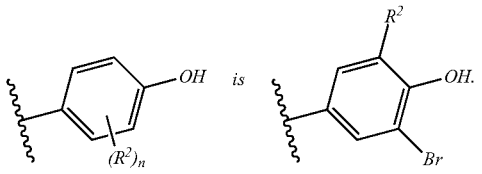

*12. A compound having the following structure:*

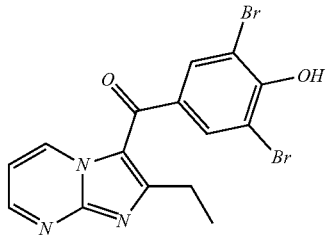

*or pharmaceutically acceptable salt thereof.*

*13. The compound of claim 4, having the Formula II-B:*

*(II-B)*

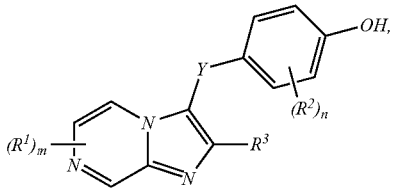

*wherein the*

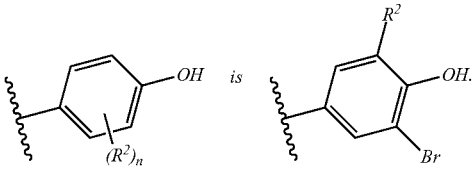

*14. A compound having the following structure:*

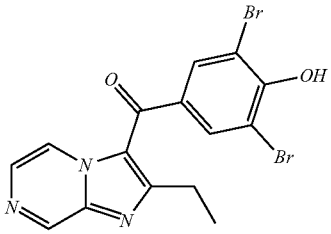

*or pharmaceutically acceptable salt thereof.*

*15. The compound of claim 4, having the Formula II-C:*

*(II-C)*

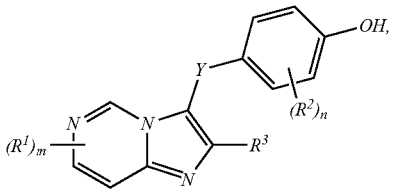

*wherein the*

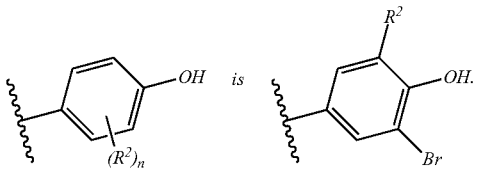

*16. The compound of claim 4, having the Formula V-B:*

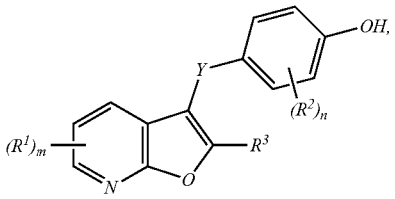

(V-B)

*wherein the*

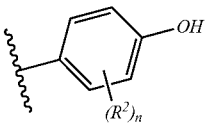

*is*

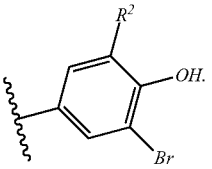

*17. The compound of claim 16, having the following structure:*

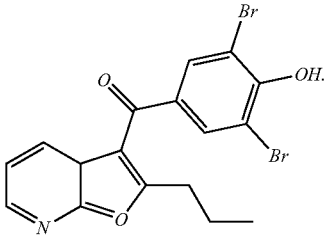

*18. A composition, comprising the compound of claim 4, a pharmaceutically acceptable salt thereof, or a hydrolyzable prodrug thereof, and a pharmaceutically acceptable excipient.*

*19. A composition, comprising the compound of claim 4 or a pharmaceutically acceptable salt thereof and a pharmaceutically acceptable carrier.*

*20. A method for treating or preventing hyperuricemia or gout, comprising administrating to a subject in need thereof a therapeutically effective amount of the compound of claim 4 or a pharmaceutically acceptable salt thereof.*

* * * * *